United States Patent
Isobe et al.

(10) Patent No.: US 8,221,398 B2
(45) Date of Patent: Jul. 17, 2012

(54) REMOTE-CONTROLLED ACTUATOR

(75) Inventors: Hiroshi Isobe, Shizuoka (JP); Yukihiro Nishio, Shizuoka (JP); Yoshitaka Nagano, Shizuoka (JP); Takayoshi Ozaki, Shizuoka (JP)

(73) Assignee: NTN Corporation, Osaka (JP)

( * ) Notice: Subject to any disclaimer, the term of this patent is extended or adjusted under 35 U.S.C. 154(b) by 0 days.

(21) Appl. No.: 13/116,679

(22) Filed: May 26, 2011

(65) Prior Publication Data

US 2011/0230868 A1    Sep. 22, 2011

Related U.S. Application Data

(63) Continuation of application No. PCT/JP2009/006286, filed on Nov. 20, 2009.

(30) Foreign Application Priority Data

Nov. 27, 2008 (JP) .................................. 2008-302091
Jan. 23, 2009 (JP) .................................. 2009-013002

(51) Int. Cl.
*A61B 17/16* (2006.01)

(52) U.S. Cl. ............................ 606/1; 606/79; 606/130

(58) Field of Classification Search ................ 606/1, 79, 606/130, 205
See application file for complete search history.

(56) References Cited

U.S. PATENT DOCUMENTS

| | | | |
|---|---|---|---|
| 4,265,231 A | 5/1981 | Scheller, Jr. et al. | |
| 4,466,429 A | 8/1984 | Loscher et al. | |
| 6,616,446 B1 | 9/2003 | Schmid | |
| 7,204,844 B2 * | 4/2007 | Jensen et al. | 606/205 |
| 8,123,740 B2 * | 2/2012 | Madhani et al. | 606/1 |
| 2002/0111635 A1 * | 8/2002 | Jensen et al. | 606/130 |
| 2005/0150123 A1 * | 7/2005 | Eaton | 33/503 |
| 2005/0192595 A1 * | 9/2005 | Green et al. | 606/130 |
| 2005/0273086 A1 * | 12/2005 | Green et al. | 606/1 |
| 2007/0213692 A1 * | 9/2007 | Neubauer et al. | 606/1 |
| 2007/0265653 A1 | 11/2007 | Suzuki | |
| 2008/0226409 A1 | 9/2008 | Hasenzahl | |

FOREIGN PATENT DOCUMENTS

| | | |
|---|---|---|
| DE | 102006030688 A1 | 4/2008 |
| JP | 60-025223 Y2 | 7/1985 |
| JP | 3-190612 A | 8/1991 |
| JP | 2558898 Y2 | 1/1998 |
| JP | 2001-017446 A | 1/2001 |
| JP | 2002-514464 A | 5/2002 |
| JP | 2007-229826 A | 9/2007 |
| JP | 2007-301149 A | 11/2007 |
| WO | 2008/072559 A1 | 6/2008 |

* cited by examiner

*Primary Examiner* — Henry M Johnson, III
(74) *Attorney, Agent, or Firm* — Pierce Atwood LLP; Kevin M. Farrell, Esq.

(57) ABSTRACT

A remote-controlled actuator includes a spindle guide section of an elongated shape, a distal end member fitted to a distal end of the spindle guide section for alteration in attitude and rotatably supporting a tool, and a drive unit housing having a base end of the spindle guide section connected therewith. A rotary shaft for transmitting rotation of a tool rotation drive source within the drive unit housing to the tool and an attitude altering member for altering the attitude of the distal end member by the drive of an attitude altering drive source within the drive unit housing are accommodated within the spindle guide section. A cutting force estimator is provided for estimating the magnitude of at least one component force of a principle force, a radial force and a feed force in a cutting force which the tool applies to a work to be processed.

15 Claims, 23 Drawing Sheets

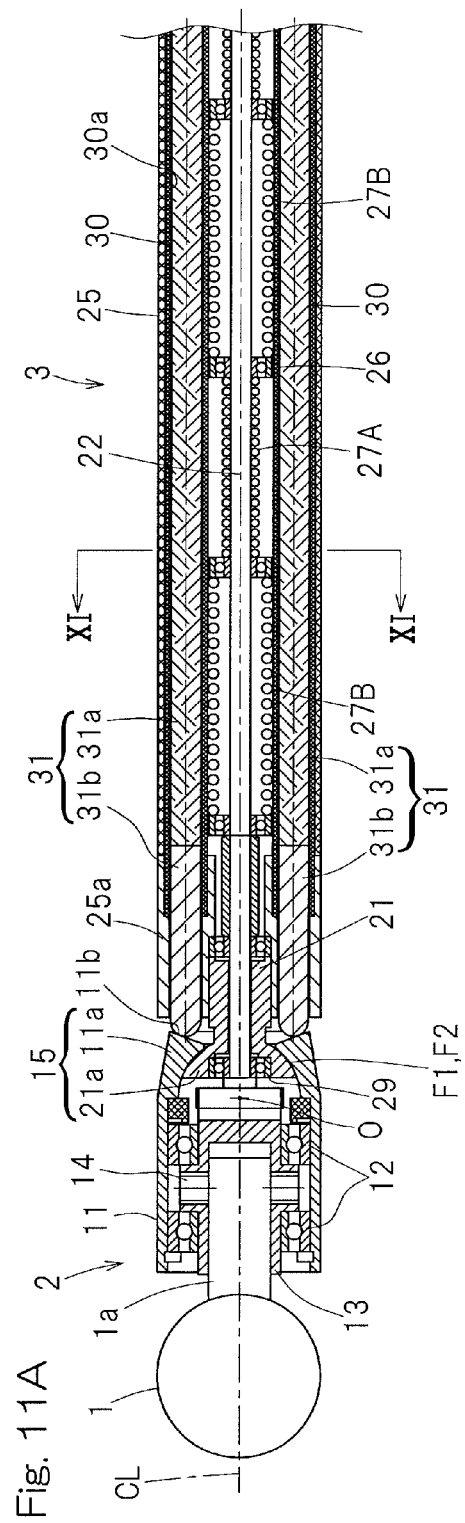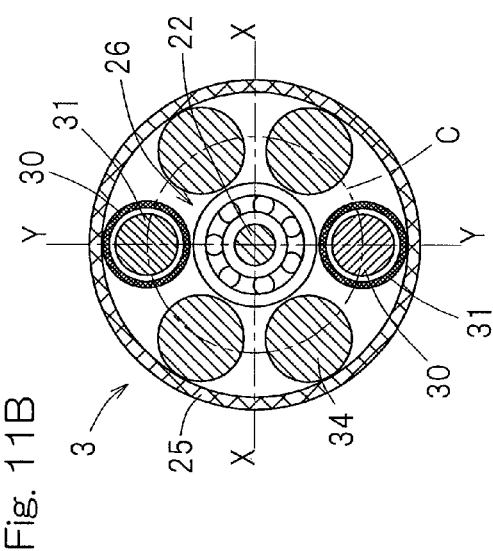
Fig. 11A
Fig. 11B

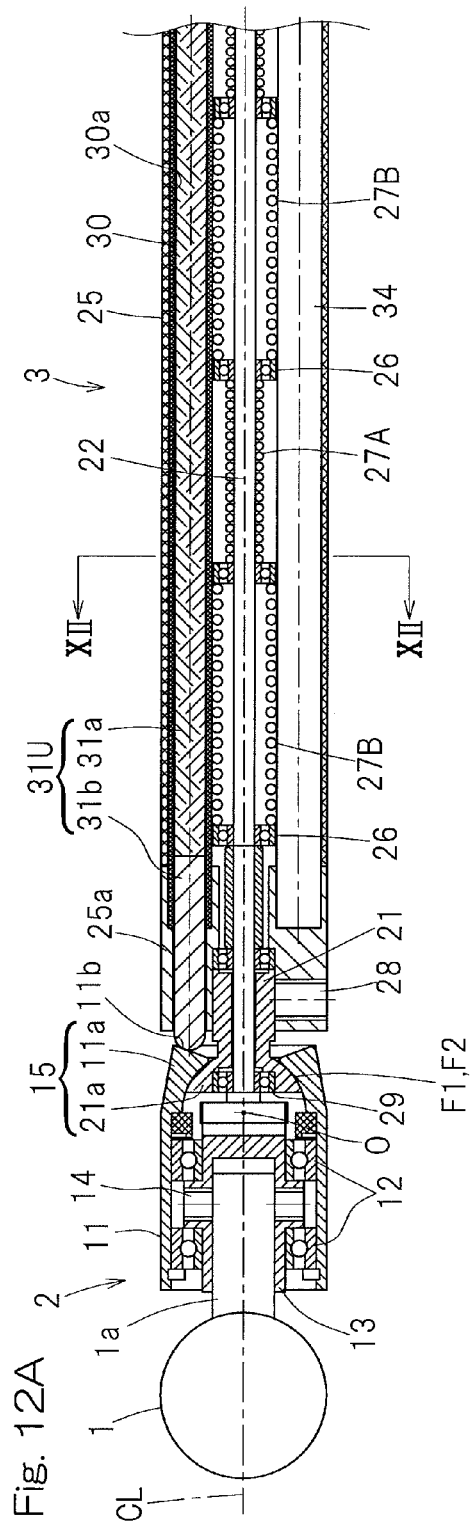
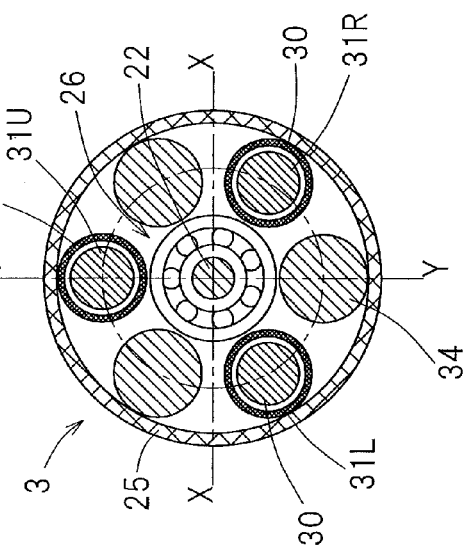
Fig. 12A
Fig. 12B

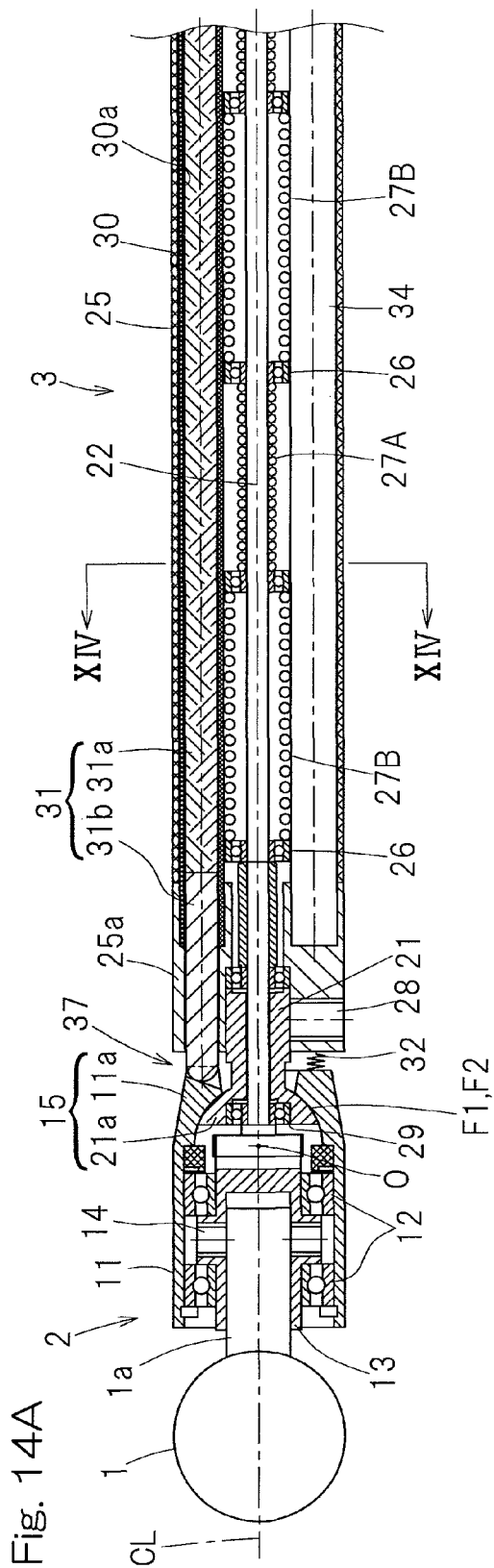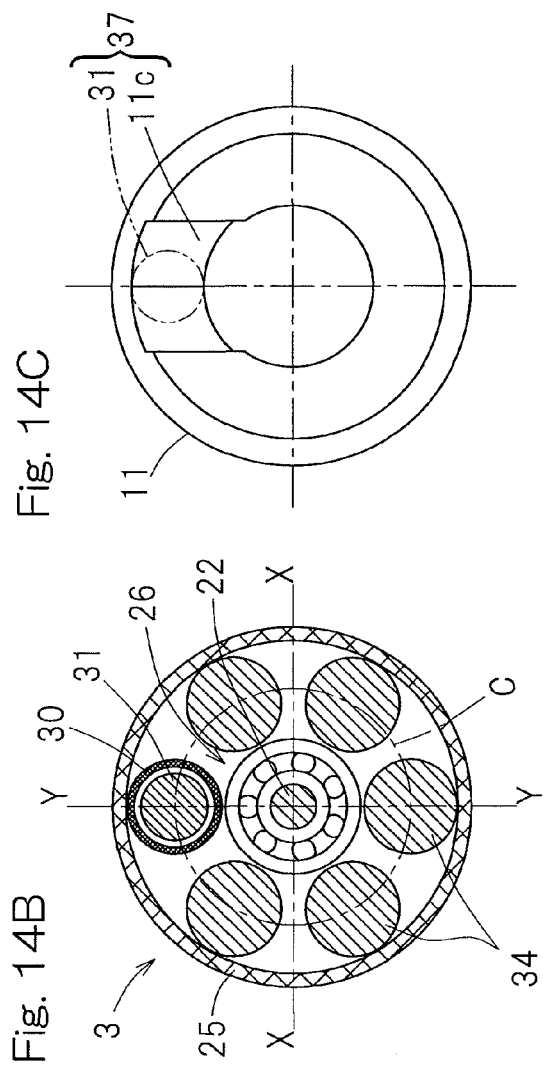
Fig. 14A
Fig. 14B
Fig. 14C

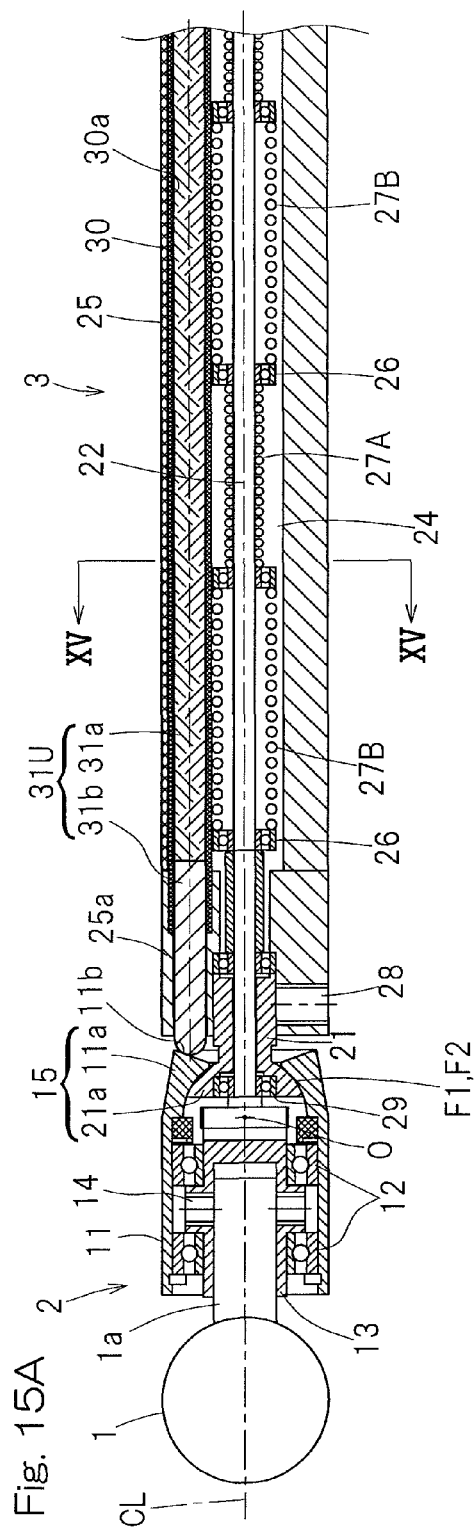
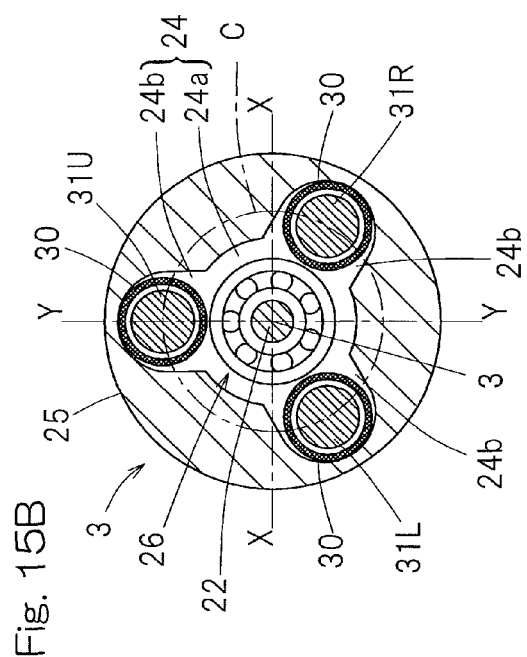
Fig. 15A
Fig. 15B

REMOTE-CONTROLLED ACTUATOR

CROSS REFERENCE TO THE RELATED APPLICATION

This application is a continuation application, under 35 U.S.C. §111(a) of international application No. PCT/JP2009/006286, filed Nov. 20, 2009, which claims priority to Japanese patent applications No. 2008-302091, filed Nov. 27, 2008, and No. 2009-013002, filed Jan. 23, 2009, the entire disclosure of both of which is herein incorporated by reference as a part of this application.

BACKGROUND OF THE INVENTION

1. Field of the Invention

The present invention relates to a remote controlled actuator for use in medical and machine processing fields and capable of changing the attitude of a machine tool.

2. Description of Related Art

Remote controlled actuators are currently available; some are used in the medical field for osteal treatment and some are used in the mechanical processing field for drilling and cutting a bone. Any of those remote controlled actuators controls by remote control a machine tool fitted to a distal end of an elongated pipe of a linear or curved configuration. However, since the conventional remote controlled actuator is designed solely to control only the rotation of the machine tool by remote control, difficulties have been encountered in processing of a complicated shape and processing at a site difficult to view with eyes from the outside in the medical field. Also, in the drilling process, the capability of processing not only the linear line, but also the curved configuration is often required. In addition, in the cutting process, the capability is required to perform the process at a site deep in grooves. In the following description, conventional art and problems inherent in the remote controlled actuator will be discussed with reference to the medical field.

In the orthopedic field, the artificial joint replacement is well known, in which a joint, of which bone has been abraded by due to bone deterioration, is replaced with an artificial joint. The joint replacement surgery requires a living bone of a patient to be processed to enable an artificial joint to be implanted. In order to enhance the strength of postoperative adhesion between the living bone and the artificial joint, such processing is required to be performed precisely and accurately in conformity to the shape of the artificial joint.

By way of example, during the hip join replacement surgery, a thigh bone is opened to secure access of an artificial joint into the femoral marrow cavity. In order to secure a strength of contact between the artificial joint and the bone, surfaces of contact of the artificial joint and the bore must be large and so the opening for insertion of the artificial joint is processed to represent an elongated shape extending deep into the bone. As a medical actuator used in cutting the bone in a manner described above, the actuator is known, in which a tool is rotatably provided in a distal end of an elongated pipe and, on the other hand, a drive source such as, for example, a motor is mounted on a proximal end of the pipe so that the tool can be driven through a rotary shaft disposed inside the elongated pipe. (See, for example, the Patent Document 1 listed below.) Since in this type of medical actuator a rotatable element that is exposed bare to the outside is only the tool at the distal end of the elongated pipe, the tool can be inserted deep into the bone.

The surgical operation for artificial joint replacement generally accompanies skin incision and muscular scission. In other words, the human body must be invaded. In order to minimize the postoperative trace, it is quite often desirable that the elongated pipe referred to above is not necessarily straight, but is moderately curved. To meet with this desire, the following technique has hitherto been suggested. For example, the Patent Document 2 listed below discloses the elongated pipe having its intermediate portion curved double to displace an axial position of the distal end of the pipe relative to the longitudinal axis of the proximal end of the same pipe. To make the axial position of the distal end of the pipe relative to the longitudinal axis of the proximal end of the same pipe is also known from other publications. Also, the Patent Document 3 listed below discloses the elongated pipe rotated 180°.

PRIOR ART LITERATURE

[Patent Document 1] JP Laid-open Patent Publication No. 2007-301149
[Patent Document 2] U.S. Pat. No. 4,466,429
[Patent Document 3] U.S. Pat. No. 4,265,231
[Patent Document 4] JP Laid-open Patent Publication No. 2001-017446

If in a condition, in which the artificial joint is inserted into an artificial joint insertion hole formed in the living bone, a large gap exist between the living bone and the artificial joint, a large length of time is required to accomplish the postoperative adhesion between the living bone and the artificial joint and, therefore, it is considered desirable that the gap should be as small as possible. Also, it is important that respective surfaces of contact between the living bone and the artificial joint be smooth, and accordingly, a high precision is required in processing the artificial joint insertion hole. Whatever the pipe take any shape, the working range of the tool is limited by the shape of the pipe and, therefore, it is difficult to widen the working range of the tool to process the artificial joint insertion hole so that the living bone and the artificial joint may can have smooth contact surfaces and, yet, the gap between the living bone and the artificial joint may be small while skin incision and muscular scission are minimized at the same time.

In general, it is quite often that the patient's bone, where an artificial joint is to be implanted, exhibits a strength lowered as a result of aging and, in a certain case, the bone itself is deformed. Accordingly, the processing of the artificial joint insertion hole is more difficult to achieve than generally considered.

In view of the foregoing, the applicant or assignee of the present invention has attempted to provide a remote controlled actuator of a type, in which the attitude of the tool coupled to the distal end can be changed by remote control so that the processing of the artificial joint insertion hole can be relatively easily and accurately performed. This is because if the attitude of the tool can be changed, the tool can be maintained at a proper attitude regardless of the shape of the pipe. It has, however, been found that since the tool is connected to the distal end of the elongated pipe, disposition of a mechanism for changing the attitude of the tool is considerably limited and, therefore, artifices are required to overcome those limitations. Also, even when the attitude of the tool is to be handled by remote control, optimum processing conditions in accord with conditions of a to-be-processed article or work are required at all times.

It is to be noted that in the case of the medical actuator having no elongated pipe used therein, a portion where the tool is mounted can change its attitude relative to a portion to be gripped by hand (See, for example, the Patent Document 4 listed above.), but nothing has yet been suggested in the art that the attitude of the tool can be changed by remote control.

SUMMARY OF THE INVENTION

An object of the present invention is to provide a remote control actuator of a type, in which the attitude of the tool coupled to the distal end of the elongated pipe section can be changed by remote control and which is capable of performing a processing under an optimum condition at all times and, also, a remote controlled actuator capable of halting the rotation of the tool or inhibiting the tool from being rotated in the event of occurrence of an abnormality.

A remote controlled actuator designed in accordance with the present invention includes a spindle guide section of an elongated configuration, a distal end member fitted to a distal end of the spindle guide section through a distal end member connecting unit for alteration in attitude, and a drive unit housing having a base end of the spindle guide section connected therewith, in which the distal end member rotatably supports a spindle for holding a tool; the spindle guide section includes a rotary shaft for transmitting rotation of a tool rotation drive source, provided within the drive unit housing, to the spindle and a guide hole open defined therein so as to extend from one end to the opposite end; an attitude altering member for altering the attitude of the distal end member as a tip end thereof selectively advances or retracts in contact with the distal end member is reciprocally movably inserted within the guide hole; and an attitude altering drive source for selectively advancing or retracting the attitude altering member is provided within the drive unit housing; and in which there is provided a cutting force estimator for estimating at least one component force of a cutting force which the tool applies to a work to be processed. The one component force is a principle force, a radial force or a feed force in the cutting force.

According to the above construction, as a result of rotation of the tool fitted to the distal end member, cutting of a bone or the like take place. In such case, when the attitude altering member is selectively advanced and retracted one at a time by the attitude altering drive source, the tip end of the attitude altering member works on the distal end member to allow the attitude of the distal end member, fitted to the tip end of the spindle guide section through the distal end member connecting unit for alteration in attitude, to alter. The attitude altering drive source is provided within the drive unit housing on the side of a base or proximate end of the spindle guide section and the alteration of the attitude of the distal end member is carried out by remote control. Since the attitude altering member is passed through the guide hole, the attitude altering member can work on the distal end member properly at all times without being displaced in a direction transverse to the longitudinal direction thereof, and the operation to alter the attitude of the distal end member takes place accurately.

The cutting force estimator estimates at least one component force of the principle force Fc, the radial force Fr and the feed force Pf in the cutting force. When processing conditions including, for example, the number of revolutions of the tool and the feed speed are properly set in dependence on the magnitude of the estimated component force, an exact processing that suits to a state of a work to be processed can be accomplished. For example, it is generally said that in cutting the bone, the bone tissue will break down when a surface being ground is heated to a temperature in excess of 50° C. Accordingly, in the case of the bone processing in the medical field, it is possible to suppress an undesirable increase of the temperature of the surface being ground when the processing conditions are changed by monitoring the cutting force with the use of the cutting force estimator.

In the present invention, the remote controlled actuator of the type referred to above may also include a driving power measuring section for measuring a driving power of the tool rotation drive source and a rotational speed measuring section for measuring the number of revolutions, in which case the cutting force estimator estimates the magnitude of the at least one component force of the principle force, the radial force and the feed force in the cutting force, from the driving power, measured by the driving power measuring section, and the number of revolutions measured by the rotational speed measuring section.

In this case, the magnitude of the principle force Fc [N], which is a component force acting in the tangential direction of the tool in the cutting force, that is, in a cutting direction, is estimated by the cutting force estimator. When the electric driving power is expressed by P [W], the number of revolutions of the tool is expressed by N [rpm] and the torque acting on the tool is expressed by T [Nm], such a relational as expressed by $P=(2\pi NT)/60$ establishes. Since the torque $T=r \cdot Fc$ when the radius of the tool is expressed by r [m], Fc will be $(60P)/(2\pi Nr)$ and, accordingly, the magnitude of the principle force Fc can be estimated by means of this relation. If the ratio of the principle force Fc, the radial force Fr and the feed force Pf is fixed, it is recommended to simultaneously utilize the cutting force estimator capable of estimating the magnitude of each of the other component forces Fr and Pf. If the ratio of those component forces changes, it is recommended to concurrently use a cutting force estimator for estimating the magnitude of each of the other component forces Fr and Pf.

In the present invention, the remote controlled actuator of the type referred to above may further include a flexure amount measuring section for measuring the amount of flexure taking place in the spindle guide section, in which case the cutting force estimator estimates the magnitude of the at least one component force of the principle force, the radial force and the feed force in the cutting force, from the amount of flexure measured by the flexure amount measuring section.

In this case, the magnitude of the radial force Fr, which is a component force acting mainly in a direction radially of the tool in the cutting force, is estimated by the cutting force estimator. The spindle guide section fluxes when the radial force Fr from the tool acts on the work to be processed, and therefore, measurement of the amount of flexure of the spindle guide section accomplished by a flexure amount measuring section makes it possible to estimate the magnitude of the radial force Fr. If the ratio of the respective magnitudes of the principle force Fc, the radial force Fr and the feed force Pf is fixed, determination of the magnitude of the radial force Fr makes it possible to estimate the respective magnitudes of the other two component forces Fc and Pf. On the other hand, if the ratio of such magnitudes changes, it is recommended to concurrently use a cutting force estimator for estimating the respective magnitudes of the other component forces Fc and Pf.

The flexure amount measuring section referred to above may include one or more strain sensor pasted to a peripheral surface of the spindle guide section.

Once the spindle guide section fluxes a strain is induced in a peripheral surface of the spindle guide section, and therefore, it is possible to measure the amount of flexure of the spindle guide section from a detection value of the strain sensor. Where a strain sensor is used as the flexure amount measuring section, the radial force Fr from the tool acts on the work to be processed, so that a detection signal of the strain sensor on the peripheral surface of the spindle guide section changes in a compressive direction or in a tensile direction depending on the direction of flexure, and therefore, the magnitude of the radial force Fr can be estimated. Also, when the feed force Pf from the tool, which is a component force acting in the axial direction of the tool in the cutting force, acts on the work to be processed, the strain sensor situated at any peripheral position on the peripheral surface of the spindle guide section generates a detection signal that changes in the compressive direction, and therefore, the magnitude of the feed component force Pf can also be estimated.

In the present invention the remote controlled actuator of the type referred to above may still include a driving power measuring section for measuring a driving power of the attitude altering drive source; and wherein the cutting force estimator estimates the magnitude of the at least one component force of the principle force, the radial force and the feed force in the cutting force, from the driving power measured by the driving power measuring section.

In this case, the magnitude of the radial force Fr, which is a force acting mainly in a direction radially of the tool in the cutting force, is estimated by the cutting force estimator. When the radial force Fr from the tool acts on the work to be processed, such a force is transmitted also to the attitude altering drive source through the attitude altering member, so that the driving power of the attitude altering drive source is increased or decreased, and therefore, measurement of the driving power with the driving power measuring section makes it possible to estimate the magnitude of the radial force Fr.

Where the remote controlled actuator of the type referred to above makes use of a lever mechanism for transmitting a driving power of the attitude altering drive source to the attitude altering member, the use may be made of a strain detector (strain sensor) for detecting a strain appearing in the lever mechanism, so that the cutting force estimator can estimate the magnitude of the at least one component force of the principle force, the radial force and the feed force in the cutting force, from a detection value of the strain detector (strain sensor).

In this case, the magnitude of the radial force Fr, which is a force acting mainly in a direction radially of the tool in the cutting force, is estimated by the cutting force estimator. When the radial force Fr from the tool acts on the work to be processed, such a force is transmitted also to the lever mechanism through the attitude altering member, accompanied by a strain occurring in the lever mechanism, and therefore, detection of the strain with the strain detector (strain sensor) makes it possible to estimate the magnitude of the radial force Fr.

In the present invention, where the remote controlled actuator of the type referred to above makes use of a plurality of rolling bearings for rotatably supporting the rotary shaft within the spindle guide section, a spring elements for applying a preload to those rolling bearings may be interposed between the neighboring rolling bearings.

In order to improve the processing finish, the spindle has to be rotated at a high speed. If the spindle is rotated at a high speed, an effect can also be appreciated that the cutting resistance to the tool can be reduced. Since the rotating force is transmitted to the spindle through the rotary shaft, made of a wire or the like, that is thin, the preload needs to be applied to the rolling bearings supporting the rotary shaft in order to realize a high speed rotation of the spindle. If the spring elements for applying the preload are provided between the neighboring rolling bearings, the spring element can be provided with no need to increase the diameter of the spindle guide section.

In the present invention, the remote controlled actuator of the type referred to above may furthermore includes an abnormality detector for detecting an abnormality occurring during the rotation or non-rotation of the spindle, and a tool rotation control section for halting the rotation of the tool rotation drive source in the event that the abnormality detector detects the abnormality.

According to the construction described above, in the event of occurrence of an abnormality during the cutting process, the abnormality detector detects the occurrence of such abnormality and the tool rotation control section then halts the rotation of the tool rotation drive source. Also, in the event that any abnormality is found by the abnormality detector prior to the cutting process taking place, the tool rotation control section inhibits the tool rotation drive source from rotating.

In the present invention, as the abnormality detector there may be provided a locked state detector for detecting whether or not the attitude of the distal end member is in a locked state, in which case the tool rotation control section inhibits the tool rotation drive source from rotating in the event that the locked state detector detects that the attitude of the distal end member is not in the locked state. The locked state detector referred to above may be one or both of a strain sensor for detecting a strain occurring in a lever mechanism disposed between the attitude altering drive source and the attitude altering member and an encoder for detecting an operating position of the attitude altering drive source.

Where an excessive force acts on the attitude altering member at the time the distal end member is to be altered in attitude so as to assume the initial attitude with no external force acting on the distal end member, there is the possibility that a foreign matter is clogged between the attitude altering member and the distal end member. Also where the attitude altering member advances beyond a predetermined position at the time the attitude altering member is urged against the distal end member with the distal end member held in the initial attitude, there is the possibility that a part of the attitude altering member is missing. Since under those circumstances the attitude of the distal end member cannot be properly locked, it is dangerous to rotate the spindle. In view of the above, the locked state detector is utilized to detect whether or not the distal end member is held in a locked state and, in the event that it is not in the locked state, the tool rotation control section inhibits the tool rotation drive source from rotating. Accordingly, it is possible to avoid the danger.

The status that the excessive force has acted on the attitude altering member at the time the distal end member is to be altered in attitude so as to assume the initial attitude with no external force acting on the distal end member can be estimated from the output of the strain sensor. Also, the status that the attitude altering member has advanced beyond the predetermined position at the time the distal end member is to be altered in attitude so as to assume the initial attitude with no external force acting on the distal end member can be estimated from the output of the encoder. Thus, by the utilization of the respective outputs of the strain sensor and the encoder, it is possible to detect whether or not the attitude of the distal end member is held in the locked state, even without the attitude of the distal member being actually measured.

In the present invention, as the abnormality detector there may be provided a working force detector for detecting the magnitude of a force acting on the distal end member during the rotation of the spindle, in which case the tool rotation control section inhibits the tool rotation drive source from rotating in the event that the working force detected by the working force detector is higher than a prescribed working force. The working force detector referred to above may be in the form of, for example, a strain sensor for detecting a strain occurring in a lever mechanism disposed between the attitude altering drive source and the attitude altering member.

If an excessive force acts on the distal end member during the rotation of the spindle, there is the possibility that various parts of the remote controlled actuator may be deformed and/or damaged. In view of the above, if the magnitude of the force acting on the distal member is detected by the working force detector and the detected working force is found exceeding the prescribed working force, the tool rotation control section halts the rotation of the tool rotation drive source. By so doing, it is possible to avoid an undesirable deformation of and/or damage to the remote controlled actuator. Thus, even though the working force on the distal end member is not actually measured, detection of the strain in the lever mechanism with the strain sensor makes it possible to facilitate determination of the working force on the distal end member.

In the present invention, as the abnormality detector there may be provided a rotation detector for detecting the number of revolutions of the spindle or the tool rotation drive source, in which case the tool rotation control section inhibits the tool rotation drive source from rotating in the event that the difference between the number of revolutions, detected by the rotation detector, and a prescribed number of revolutions is out of a predetermined range. The rotation detector referred to above may be in the form of, for example, a rotational speed sensor for detecting the number of revolution of the tool rotation drive source.

In the event that the output shaft of the tool rotation drive source and/or the bearing for supporting the rotary shaft for transmitting the rotation of the tool rotation drive source to the spindle fail to operate properly, the number of revolutions of the spindle may abnormally increase or decrease. It is dangerous to allow the spindle to continue its rotation under such a condition. Accordingly, if the number of revolutions of the spindle is detected by the rotation detector and the difference between the detected number of revolutions and the prescribed number of revolutions is found out of the predetermined range, the tool rotation control section halts the rotation of the tool rotation drive source. By so doing, it is possible to avoid the danger. Thus, even though the number of revolutions of the spindle is not actually detected, detection of the number of revolutions of the tool rotation drive source with the rotation detector makes it possible to easily determine the number of revolutions of the spindle.

In the present invention, as the abnormality detector there may be provided a vibration detector for detecting the magnitude of vibration of the tool rotation drive source or the spindle during the rotation of the spindle, in which case the tool rotation control section inhibits the tool rotation drive source from rotating in the event that the magnitude of the vibration detected by the vibration detector is larger than a prescribed magnitude. The vibration detector may be in the form of, for example, a vibration sensor.

In the event of occurrence of a reduction in attitude holding force of the distal end member, a trouble in the tool rotation drive source and/or the bearing, or a defect in assemblage of the remote controlled actuator, the spindle undergoes oscillation. As a matter of course, it is dangerous to allow the spindle to continue its rotation under such a condition. Accordingly, if the magnitude of oscillation of the spindle is detected by the vibration detector and the magnitude of the vibration so detected is higher than the prescribed magnitude, the tool rotation control section halts the rotation of the tool rotation drive source. In this way, the danger can be avoided.

In the present invention, as the abnormality detector there may be provided a temperature detector for detecting the temperature of the spindle during the rotation of the spindle, in which case the tool rotation control section inhibits the tool rotation drive source from rotating in the event that the temperature detected by the temperature detector is higher than a prescribed temperature.

It may occur that the temperature of the spindle will increase as a result of the lack of a lubricant for lubricating the bearing or a trouble occurring in the bearing. In such case, if the spindle continue its rotation as it stands, deformation and/or damage would result in the remote controlled actuator. Accordingly, if the temperature of the spindle is detected by the temperature detector and the detected temperature is higher than the prescribed temperature, the tool rotation control section halts the tool rotation drive source. In this way, it is possible to avoid the deformation of and/or damage to the remote controlled actuator.

In the present invention, the remote controlled actuator may still further include a bearing for rotatably supporting the rotary shaft within the spindle guide section, a liquid lubricant supply device for supplying a liquid lubricant for lubricating the bearing to the inside of the spindle guide section, and a liquid lubricant pressure detector, as the abnormality detector, for detecting the pressure of the liquid lubricant supplied by the liquid lubricant supply device to the inside of the spindle guide section during the rotation of the spindle, in which case the tool rotation control section inhibits the tool rotation drive source from rotating in the event that the difference between the pressure of the liquid lubricant, detected by the liquid lubricant pressure detector, and a prescribed pressure is out of a predetermined range.

When the bearing for rotatably supporting the rotary shaft within the spindle guide section is to be lubricated with the liquid lubricant supplied from the liquid lubricant supply device to the inside of the spindle guide section, the lack of the liquid lubricant will result in lowering of the pressure of the liquid lubricant or clogging occurring in the path of travel of the liquid lubricant will result in increase of the pressure of the liquid lubricant. The lack of the liquid lubricant and the clogging in the path hamper a favorable lubrication of the bearing and, therefore, there is the risk that the bearing may be damaged. Accordingly, if the pressure of the liquid lubricant is detected by the liquid lubricant pressure detector and the difference between the detected pressure and the prescribed pressure is found out of the predetermined range, the tool rotation control section halts the rotation of the tool rotation drive source. In this way the possible damage to the bearing can be avoided.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 11A is a sectional view showing the distal end member and the spindle guide section, both employed in the remote controlled actuator according to a second preferred embodiment of the present invention;

FIG. 11B is a cross sectional view taken along the line XI-XI in FIG. 11A;

FIG. 12A is a sectional view showing the distal end member and the spindle guide section, both employed in the remote controlled actuator according to a third preferred embodiment of the present invention;

FIG. 12B is a cross sectional view taken along the line XII-XII in FIG. 12A;

FIG. 14A is a sectional view showing the distal end member and the spindle guide section, both employed in the remote controlled actuator according to a fourth preferred embodiment of the present invention;

FIG. 14B is a cross sectional view taken along the line XIV-XIV in FIG. 14A;

FIG. 14C is a view of a housing for the distal end member as viewed from a base end side;

FIG. 15A is a sectional view showing the distal end member and the spindle guide section, both employed in the remote controlled actuator according to a fifth preferred embodiment of the present invention;

FIG. 15B is a cross sectional view taken along the line XV-XV in FIG. 15A;

DESCRIPTION OF PREFERRED EMBODIMENTS

Figure 1:
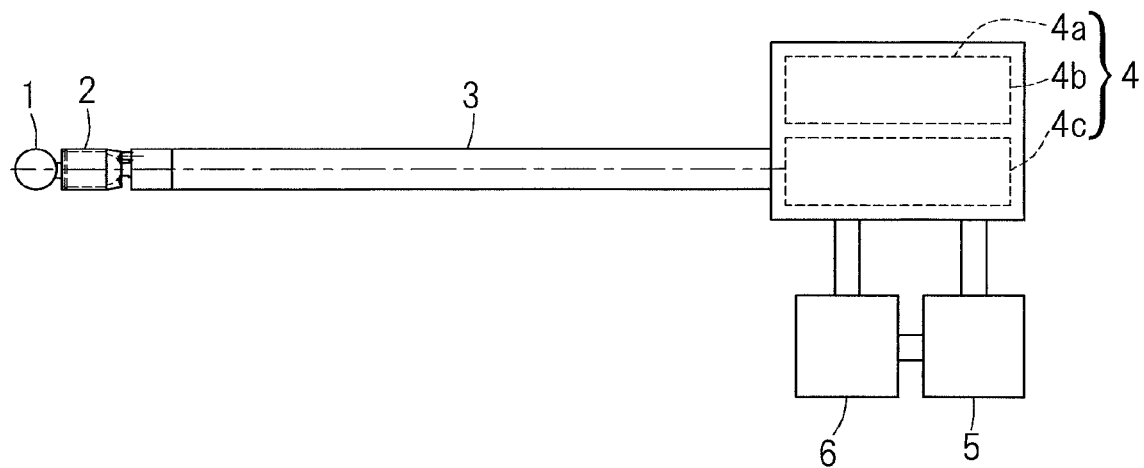
FIG. 1 is a diagram showing a schematic construction of a remote controlled actuator according to a first preferred embodiment of the present invention.

A first preferred embodiment of the present invention will now be described with particular reference to FIG. 1 to FIGS. 3A and 3B. Referring to FIG. 1, a remote controlled actuator according to the first embodiment of the present invention includes a distal end member 2 for holding a rotary tool 1, an elongated spindle guide section 3 having a distal end to which the distal end member 2 is coupled for displacement in attitude, a drive unit housing 4a to which a proximal end of the spindle guide section 3 is coupled, a controller 5 for controlling a tool rotating drive mechanism 4b and an attitude altering drive mechanism 4c, both accommodated within the drive unit housing 4a, and a cutting force estimator 6 for estimating a cutting force during the processing. The drive unit housing 4a cooperates with the built-in tool rotating drive mechanism 4b and attitude altering drive mechanism 4c to form a drive unit 4.

Figure 2A:
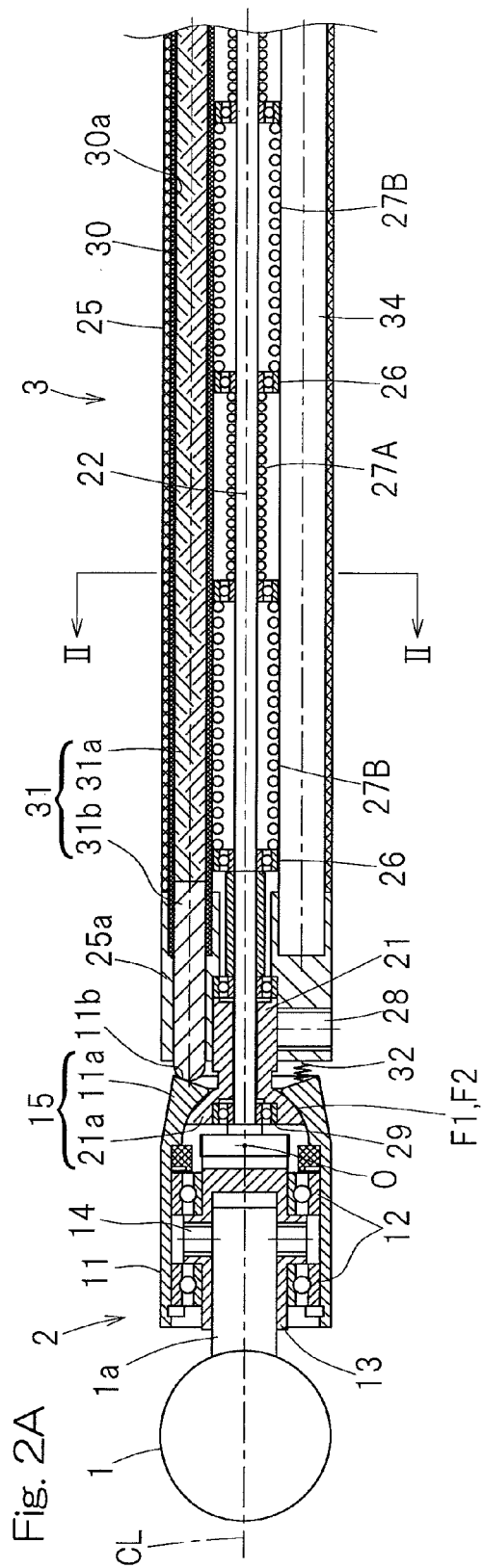
FIG. 2A is a sectional view showing a distal end member and a spindle guide section both employed in the remote controlled actuator.
Figure 2C:
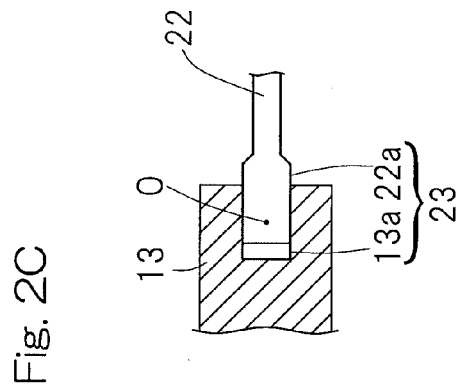
FIG. 2C is a diagram showing a connecting unit between the distal end member and a rotary shaft.
Figure 2B:
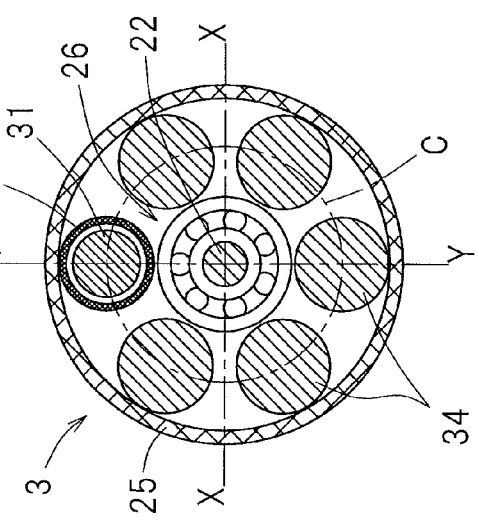
FIG. 2B is a cross sectional view taken along the line II-II in FIG. 2A.

As best shown in FIGS. 2A to 2C, the distal end member 2 includes a generally or substantially cylindrical housing 11 and a spindle 13 rotatably accommodated within such cylindrical housing 11 through a pair of bearings 12. The spindle 13 is of a tubular shape having a distal side opening and having a hollow defined therein, and a tool 1 is drivingly coupled with the spindle 13. Specifically, a shank portion 1a of the tool 1 is inserted into the hollow of the spindle 13 and is then coupled with such spindle 13 by means of a stop pin 14 for rotation together with the spindle 13. The distal end member 2 of the structure described above is coupled with a distal end of the spindle guide section 3 through a distal end member connecting unit 15. The distal end member connecting unit 15 is means for supporting the distal end member 2 for displacement in attitude and is comprised of a spherical bearing. More specifically, the distal end member connecting unit 15 includes a guided member 11a in the form of an inner diameter reduced portion at a base end of the housing 11, and a guide member 21a in the form of a collar integral with a constraint member 21 fixed to the tip of the spindle guide section 3. The guided member 11a and the guide member 21a have respective guide faces F1 and F2 that are held in sliding contact with each other, and those guide faces F1 and F2 have respective centers of curvature lying at a point O on the center line or longitudinal axis CL of the spindle 13, having their diameters being reduced towards the base end of the spindle 13. Accordingly, not only can the distal end member 2 be immovably constrained relative to the spindle guide section 3, but it can also be supported for displacement in attitude so that the attitude of the distal end member 2 can be altered. It is to be noted that since in this example, the distal end member 2 can have its attitude altered about a lateral X-axis passing through the center of curvature O, the guide faces F1 and F2 may be a cylindrical surface having a longitudinal axis represented by the X-axis passing through the center of curvature O.

Figure 3A:
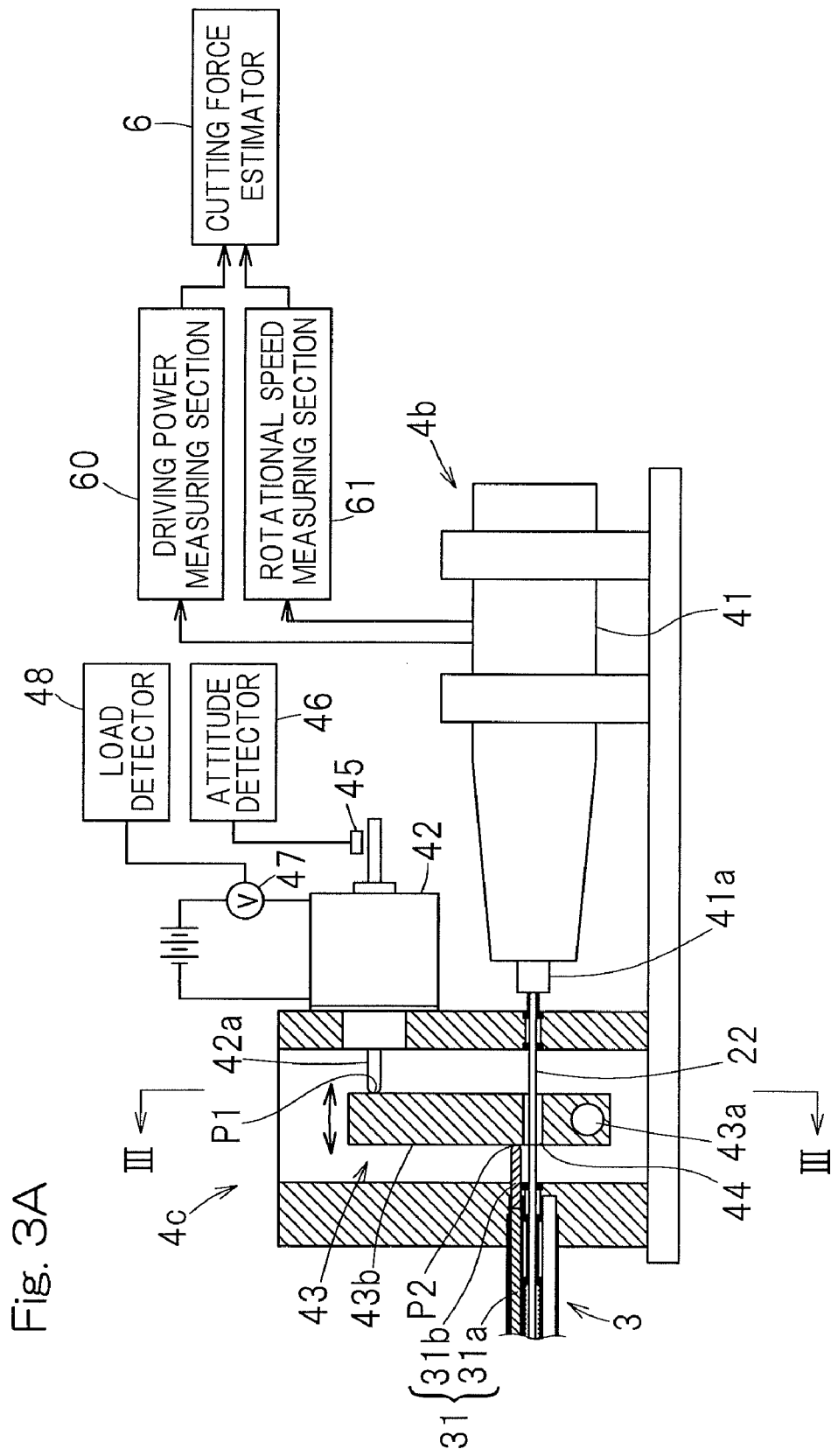
FIG. 3A is a diagram illustrating a sectional view of a tool rotation drive mechanism and an attitude alteration drive mechanism, both employed in the remote controlled actuator, shown together with a control system therefor.
Figure 3B:
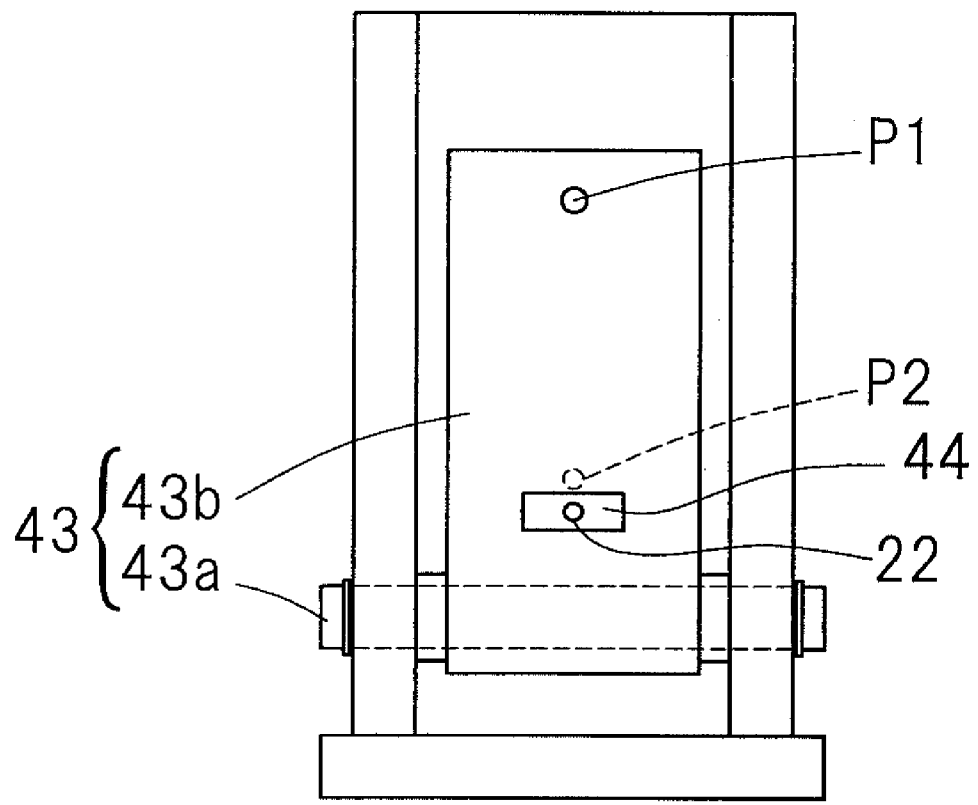
FIG. 3B is a cross sectional view taken along the line III-III in FIG. 3A.

The spindle guide section 3 includes a rotary shaft 22 for transmitting a rotational force exerted by a tool rotation drive source 41 accommodated within the drive unit housing 4a (FIGS. 3A and 3B). In the illustrated example, the rotary shaft 22 is employed in the form of a wire capable of undergoing deformation to a certain extent. Material for the wire includes, for example, metal, resin or glass fiber. The wire may be either a single wire or a stranded wire. As best shown in FIG. 2C, the spindle 13 and the rotary shaft 22 are connected together by means of an universal joint 23 for transmitting rotation from the rotary shaft 22 to the spindle 13. The universal joint 23 is made up of a groove 13a, defined in a closed base end of the spindle 13, a projection 22a defined in a distal end of the rotary shaft 22 and engageable in the groove 13a. The center of joint between the groove 13a and the projection 22a is located at the same position as the centers of curvature O of the guide faces F1 and F2.

The spindle guide section 3 includes an outer shell pipe 25 forming an outer shell of the spindle guide section 3 and the rotary shaft 22 referred to above is positioned at the center of this outer shell pipe 25. The rotary shaft 22 so positioned is rotatably supported by a plurality of rolling bearings 26 positioned spaced a distant apart from each other in a direction axially of the spindle guide section 3. Spring elements 27A and 27B for generating a preload on the corresponding rolling bearing 26 are disposed between the neighboring rolling bearings 26. Each of those spring elements 27A and 27B is employed in the form of, for example, a compression spring. There are the spring element 27A for inner ring for generating the preload on the inner ring of the rolling bearing 26 and the spring element 27B for outer ring for generating the preload on the outer ring of the rolling bearing 26, and the both are arranged alternately relative to each other. The constraint member 21 referred to previously is fixed to a pipe end portion 25a of the outer shell pipe 25 by means of a fixing pin 28 and has its distal end inner peripheral portion supporting the distal end of the rotary shaft 22 through a rolling bearing 29. It is, however, to be noted that the pipe end portion 25a may be a member separate from the outer shell pipe 25 and may then be connected with the outer shell pipe 25 by means of, for example, welding.

A single guide pipe 30 open at opposite ends thereof is provided between an inner diametric surface of the outer shell pipe 25 and the rotary shaft 22, and an attitude altering member 31, made up of a wire 31a and pillar shaped pins 31b at opposite ends, is axially movably inserted within a guide hole 30a, which is an inner diametric hole of the guide pipe 30. One of the pillar shaped pins 31b, which is on the side of the distal end member 2, has its tip representing a spherical shape and is held in contact with a base end face of the distal end member housing 11. The base end face 11b of the housing 11 for the distal end member 2 is so shaped as to represent an inclined face such that an outer peripheral edge thereof is closer to the spindle guide section 3 than a center portion thereof Similarly, the other of the pillar shaped pins 31b, that is, the pillar shaped pin 31b on the side of the drive unit housing 4a has its tip representing a spherical shape and held in contact with a side face of a lever 43 (FIGS. 3A and 3B) as will be described in detail later.

It is to be noted that the use of the pillar shaped pins 31b may be dispensed with, leaving only the signal wire 31a to constitute the attitude altering member 31.

At a position spaced 180° in phase from a peripheral position where the attitude altering member 31 referred to above is positioned, a restoring elastic member 32, which is in the form of, for example, a compression spring, is provided between the base end face of the housing 11 for the distal end member 2 and a tip end face of the outer shell pipe 25 of the spindle guide section 3. This restoring elastic member 32 has a function of biasing the distal end member 2 towards the side of a predetermined attitude.

Also, between the inner diametric surface of the outer shell pipe 25 and the rotary shaft 2, a plurality of reinforcement shafts 34 are arranged separate from the guide pipe 30 and on the pitch circle C of the same diameter as the guide pipe 30. Those reinforcement shafts 34 are used to secure the rigidity of the spindle guide section 3. The guide pipe 30 and the reinforcement shafts 34 are arranged equidistantly relative to each other around the rotary shaft 22. The guide pipe 30 and the reinforcement shafts 34 are held in contact with the inner diametric surface of the outer shell pipe 25 and respective outer peripheral surfaces of the rolling bearings 26. In this manner, the outer diametric surfaces of those rolling bearings 26 are supported.

The tool rotating drive mechanism 4b and the attitude altering drive mechanism 4c, both housed within the drive unit housing 4a, are best shown in FIGS. 3A and 3B.

The tool rotating drive mechanism 4b makes use of a tool rotation drive source 41 that is controlled by the controller 5. This tool rotation drive source 41 is in the form of, for example, an electric motor, having its output shaft 41a coupled with a base end or proximal end of the rotary shaft 22.

The electric driving power and the number of revolutions of the tool rotation drive source 41 are measured by a driving power measuring section 60 and a rotational speed measuring section 61, respectively. The driving power measuring section 60 is comprised of, for example, a power meter provided in an electric source system (not shown) of the tool rotation drive source 41. The rotational speed measuring section 61 is comprised of, for example, a rotary encoder or a tachometer. Respective output signals of the driving power measuring section 60 and the rotational speed measuring section 61 are supplied to the cutting force estimator 6. This cutting force estimator 6 is operable to estimate a cutting force of the tool 1 from the respective output signals of the driving power measuring section 60 and the rotational speed measuring section 61. The cutting force estimator 6 is comprised of a computer such as, for example, a microcomputer, or an electronic circuit and includes a relation setting module (not shown), in which relations between the respective input signals and estimated values, which will become an output signal, are set in terms of calculating equations and/or tables so that the estimated value can be estimated by comparing the input signal with the relation setting module. It is to be noted that various cutting force estimator 6, which will be hereinafter referred to in this specification, are also comprised of a computer or an electronic circuit which utilizes the relation setting module to provide the estimated value in a manner as hereinabove described.

Figure 4A:
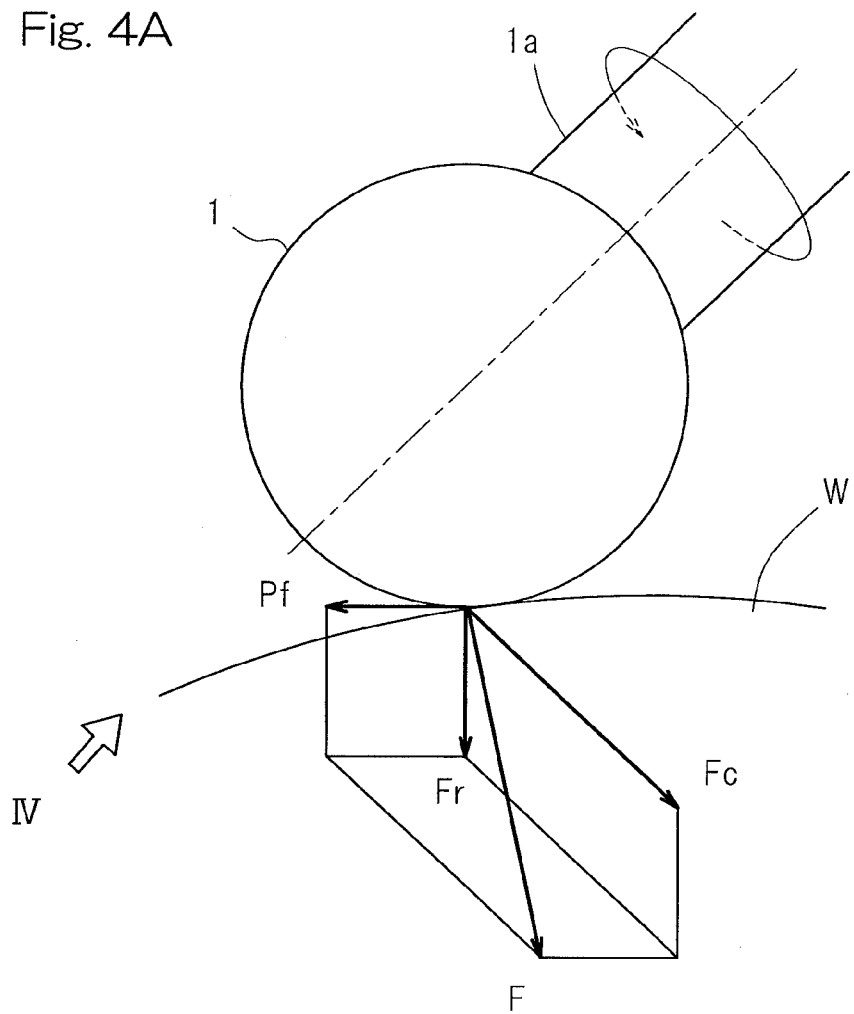
FIG. 4A is a perspective view showing a tool and a to-be-processed article during a cutting process.
Figure 4B:
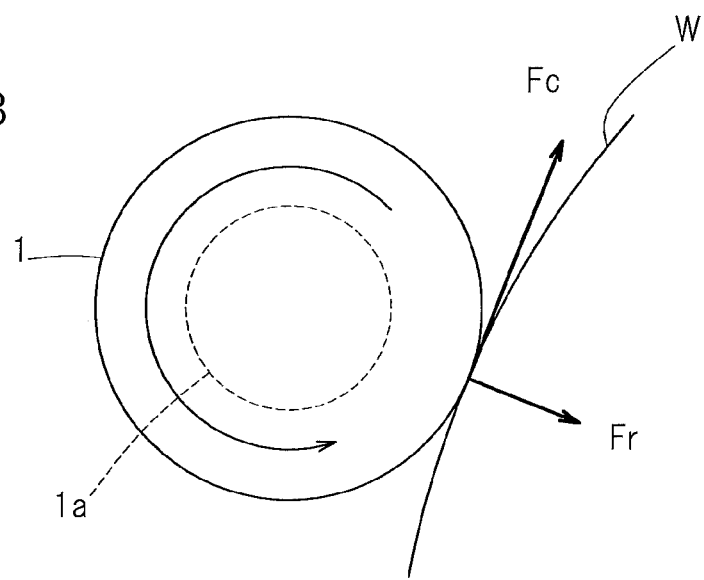
FIG. 4B is a diagram as viewed in a direction along the arrow IV in FIG. 4A.

In the case of this embodiment described above, the magnitude of a principle force for cutting or tangential force Fc [N], which is a component force acting in a tangential direction of the tool 1 at a cutting force F, which the tool 1 applies to a work W being processed, that is, in a cutting direction, is estimated by the cutting force estimator 6 (See FIGS. 4A and 4B.). Assuming that the electric driving power is expressed by P [W], the number of revolutions of the tool 1 is expressed by N [rpm] and the torque acting on the tool 1 is expressed by T [Nm], such a relational as expressed by $P=(2\pi NT)/60$ establishes. Since the torque $T=r \cdot Fc$ when the radius of the tool 1 is expressed by r [m], Fc will be $(60P)/(2\pi Nr)$ and, from this relation, the magnitude of the principle force Fc can be estimated. If the ratio of the principle force Fc, a radial force or normal force Fr and a feed force or axial force Pf is fixed, it is recommended to simultaneously utilize the cutting force estimator capable of estimating the magnitude of each of the other component forces Fr and Pf. If the ratio of the principle force Fc, the radial force Fr and the feed force Pf changes, it is recommended to concurrently use a cutting force estimator for estimating the magnitude of each of the other component forces Fr and Pf. It is to be noted that the cutting force estimator 6 may provided outside the controller 5 such as shown in FIG. 1 or inside the controller 5.

The attitude alteration drive mechanism 4c includes an attitude altering drive source 42 that is controlled by the controller 5. This attitude altering drive source 42 is in the form of, for example, an electrically operated linear actuator and had an output rod 42a capable of moving leftwards or rightwards, as viewed in FIG. 3A, the movement of such output rod 42a being transmitted to the attitude altering member 31 through a lever mechanism 43, which is a force transmitting mechanism. It is to be noted the attitude altering drive source 42 may be a rotary motor.

The lever mechanism 43 includes a pivot lever 43b pivotable about a support pin 43a and is so designed and so configured as to allow a force of the output rod 42a to work on a working point P1 of the lever 43b, which is spaced a long distance from the support pin 43a, and as to apply a force to the attitude altering member 31 at a force point P2, which is spaced a short distance from the support axis 43a, wherefore an output of the attitude altering drive source 42 can be increased and then transmitted to the attitude altering member 31. Since the use of the lever mechanism 43 is effective to enable a large force to be applied to the attitude altering member 31 even in the linear actuator of a low output capability, the linear actuator can be downsized. The rotary shaft 22 extends through an opening 44 defined in the pivot lever 43b. It is to be noted that instead of the use of the attitude altering drive source 42 or the like, the attitude of the distal end member 2 may be manually operated from a remote site (by remote control).

The attitude altering drive mechanism 4c is provided with an operating amount detector 45 for detecting the operating amount of the attitude altering drive source 42. A detection value outputted from this operating amount detector 45 is outputted to an attitude detector 46. The attitude detector 46 is operable to detect the attitude inclined about the X-axis (FIGS. 2A to 2C) of the distal end member 2, that is, to detect the attitude of the distal end member 2 that has been inclined about the X-axis. The attitude detector 46 includes a relation setting means (not shown), in which the relation between the output signal of the operating amount detector 45 and the attitude of the distal end member 2 inclined is set in terms of an arithmetic equation or table, and makes use of the relation setting means to detect the inclination in attitude in reference to the output signal inputted. This attitude detector 46 may be provided either in the controller 5 or in an external control device.

Also, the attitude altering drive mechanism 4c is provided with a supply power meter 47 for detecting the electric energy supplied to the attitude altering drive source 42, which is an electrically operated actuator. A detection value of this supply power meter 47 is outputted to a load detector 48. This load detector 48 in turn detects a load acting on the distal end member 2 in reference to an output of the supply power meter 47. This load detector 48 includes a relation setting means (not shown), in which the relation between the load and the output signal of the supply power meter 47 is set in terms of an arithmetic equation or table, and makes use of the relation setting means to detect the load in reference to the output signal so inputted. This load detector 48 may be provided either in the controller 5 or in an external control device.

The controller 5 controls the attitude altering drive source 42 on the basis of the respective detection values of the attitude detector 46 and the load detector 48 and also controls the tool rotation drive source 41 on the basis of an output of the cutting force estimator 6.

The operation of the remote controlled actuator of the construction hereinabove described will now be described in detail.

When the tool rotation drive source 41 is driven, the rotational force thereof is transmitted to the spindle 13 through the rotary shaft 22 to thereby rotate the tool 1 together with the spindle 13. The load acting on the distal end member 2 when the tool 1 then being rotated cuts a bone or the like is detected from the detection value of the supply power meter 47 by the load detector 48. Accordingly, when the amount of feed of the remote controlled actuator in its entirety and the alteration of attitude of the distal end member 2, as will be described later, are controlled in dependence on the value of the load detected in the manner described above, cutting of the bone with the load acting on the distal end member 2 can be properly carried out while the load acting on the distal end member 2 is maintained properly.

During the use, the attitude altering drive source 42 is driven to alter the attitude of the distal end member 2 by remote control. By way of example, if the attitude altering member 31 is advanced by the attitude altering drive source 42 in a direction towards the tip or distal side, the housing 11 for the distal end member 2 is pressed by the attitude altering member 31 with the distal end member 2 consequently altered in attitude along the guide faces F1 and F2 so that the tip or distal side can be oriented downwardly as viewed in FIG. 2A. If the attitude altering member 31 is conversely retracted by the attitude altering drive source 42, the housing 11 for the distal end member 2 is pressed backwardly by the effect of the elastic repulsive force exerted by the restoring elastic member 32 and, consequently, the distal end member 2 is altered in attitude along the guide faces F1 and F2 so that the tip or distal side can be oriented upwardly as viewed in FIG. 2A. At this time, a pressure from the attitude altering member 31, the elastic repulsive force from the restoring elastic member 32 and a reactive force from the constraint member 21 are applied to the distal end member connecting unit 15 and, depending on the balance of those applied forces, the attitude of the distal end member 2 is determined. The attitude of the distal end member 2 is detected by the attitude detector 46 from the detection value of the operating amount detector 45. For this reason, the attitude of the distal end member 2 can be properly controlled by remote control.

Since the base end face 11b of the housing 11 for the distal end member 2 is so shaped to represent the inclined face that the outer peripheral edge thereof may be closer towards the spindle guide section 3 than the center portion thereof, when the attitude altering member 31 pushes the base end face 11b of the housing 11, the base end face 11b of the housing 11 is apt to slip relative to the attitude altering member 31 and, therefore, a smooth alteration in attitude of the housing 11 can be accomplished. It is, however, to be noted that the base end face 11b of the housing 11 may not be necessarily so shaped as to represent the inclined face and may be so shaped as to represent an end face orthogonal to the direction of selective advance or retraction of the attitude altering member 31.

Since the attitude altering member 31 is inserted through the guide hole 30a, the attitude altering member 31 can properly act on the distal end member 2 at all times without being accompanied by displacement in position in a direction perpendicular to the lengthwise direction thereof and the attitude altering operation of the distal end member 2 can therefore be performed accurately. Also, since the attitude altering member 31 is comprised of mainly the wire 31a and has a flexible property, the attitude altering operation of the distal end member 2 is carried out accurately even though the spindle guide section 3 is curved. In addition, since the center of the junction between the spindle 13 and the rotary shaft 22 lies at the same position as the respective centers of curvature O of the guide faces F1 and F2, no force tending to press and pull will not act on the rotary shaft 22 as a result of the alteration of the attitude of the distal end member 2 and the distal end member 2 can be smoothly altered in attitude.

Also, during the cutting, the magnitude of the principle force Fc for the cutting force F is estimated by the cutting force estimator 6. When processing conditions including the number of revolutions of the tool 1 and the feed speed of the tool 1 are optimally set in dependence on the magnitude of the principle force Fc so estimated, a fine processing appropriate to the status of the work W to be processed (FIGS. 4A and 4B) can be realized. For example, it is generally said that in cutting the bone, the bone tissue will break down when a surface being ground is heated to a temperature in excess of 50° C. Accordingly, in the case of the bone processing in the medical field, it is possible to suppress an undesirable increase of the temperature of the surface being ground when the processing conditions are changed by monitoring the cutting force with the use of the cutting force estimator 6.

The remote controlled actuator of the foregoing construction is utilized in grinding the femoral marrow cavity during, for example, the artificial joint replacement surgery and during the surgery, it is used with the distal end member 2 in its entirety or a part thereof inserted into the body of a patient. Because of this, if the distal end member 2 can be altered in attitude by remote control, the bone can be processed in a condition with the tool 1 maintained in a proper attitude at all times and the opening for insertion of the artificial joint can be finished accurately and precisely.

There is the necessity that the rotary shaft 22 and the attitude altering member 31 are provided in a protected fashion. In this respect, as shown in FIG. 2B, the spindle guide section 3, which is elongated in shape, is provided with the rotary shaft 22 at the center of the outer shell pipe 25 and the guide pipe 30, accommodating therein the attitude altering member 31, and the reinforcement shafts 34, all of these are arranged in the circumferential direction and between the outer shell pipe 25 and the rotary shaft 22. Accordingly, the rotary shaft 22 and the attitude altering member 31 can be protected and the interior can be made hollow to thereby reduce the weight without sacrificing the rigidity. Also, the arrangement balance as a whole is rendered good.

Since the outer diametric surfaces of the rolling bearings 26 supporting the rotary shaft 22 are supported by the guide pipe 30 and the reinforcement shafts 34, the outer diametric surfaces of the rolling bearings 26 can be supported with no need to use any extra member. Also, since the preload is applied to the rolling bearings 26 by means of the spring elements 27A and 27B, the rotary shaft 22 comprised of the wire can be rotated at a high speed. Because of that, the processing can be accomplished with the spindle 13 rotated at a high speed and a good finish of the processing can also be obtained and the cutting resistance acting on the tool 1 can be reduced. Since the spring elements 27A and 27B are disposed between the neighboring rolling bearings 26, the spring elements 27A and 27B can be provided with no need to increase the diameter of the spindle guide section 3.

Figure 5:
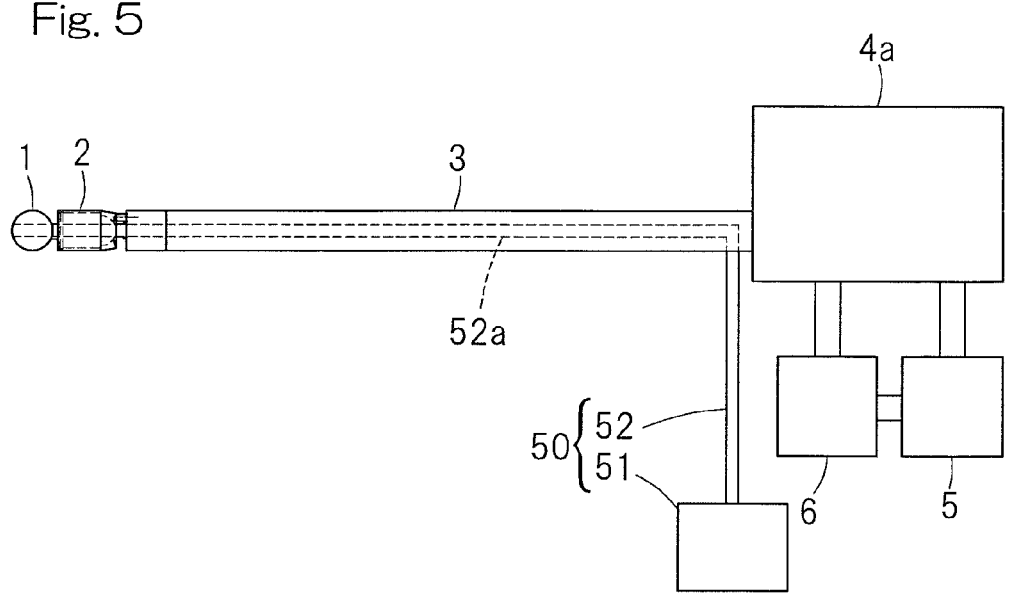
FIG. 5 is a diagram showing a schematic construction when a cooling unit is provided in the remote controlled actuator.

In view of the spindle guide section 3 being of a hollow shape, the remote controlled actuator of the present invention can be provided with a cooling unit 50 for cooling the tool 1 as shown in FIG. 5. The cooling unit 50 includes a cooling liquid supply device 51 provided outside the drive unit housing 4a and a cooling liquid supply passage 52 continuing from the cooling liquid supply device 51 to the base end of the spindle guide section 3 for supplying a cooling liquid, fed from the cooling liquid supply device 51, towards the tool 1 through respective interiors of the spindle guide section 3 and the distal end member 2. A passage portion 52a of the cooling liquid supply passage 52, which extends within the spindle guide section 3, is defined by the outer shell pipe 25 itself, which concurrently serves as the cooling liquid supply tube 52, and is designed to allow the cooling liquid to flow through the interior of the outer shell pipe 25. The cooling liquid supplied to the tool 1 is subsequently discharged to an outer periphery of the tool 1. A sealing member (not shown) is preferably provided between the spindle guide section 3 and the drive unit housing 4a for avoiding an undesirable ingress of the cooling liquid into the drive unit housing 4a.

If the cooling unit 50 is provided in this way, heat emitting areas such as, for example, the tool 1, a to-be-processed article or work W, the spindle 13, the rotary shaft 22 and the rolling bearings 26 and 29 can be cooled. Since the liquid coolant is passed through the outer shell pipe 25, there is no need to use any extra tube for the purpose of supplying the liquid coolant and the spindle guide section 3 can therefore be simplified and made small in diameter. Also, the liquid coolant may be concurrently used for lubrication of the rolling bearings 26 and 29. By so doing, the use of a grease or the like, which is generally used, can be dispensed with and, also, there is no need to use any extra lubricating device. It is to be noted that a liquid coolant recirculating system may be designed, in which the liquid coolant once guided to the tool 1 is returned to the liquid coolant supply device 51 without being discharged to the outer periphery of the tool 1. It is, however, noted that where the flow of the liquid coolant passing through the outer shell pipe 25 is small, an extra liquid coolant has to be supplied from the outside of the spindle guide section 3 to cool the tool 1 and the to-be-processed work W.

The liquid coolant referred to above is preferably in the form of water or physiological saline. If the liquid coolant is employed in the form of water or physiological saline, the liquid coolant will bring no adverse influence on the living body when the processing is performed with the distal end member 2 inserted into the living body. Where water or physiological saline is employed for the liquid coolant, component parts, with which the liquid coolant contacts, are preferably made of stainless steel that is excellent in resistance to corrosion. Any other component parts forming the remote controlled actuator may be made of stainless steel.

Figure 6A:
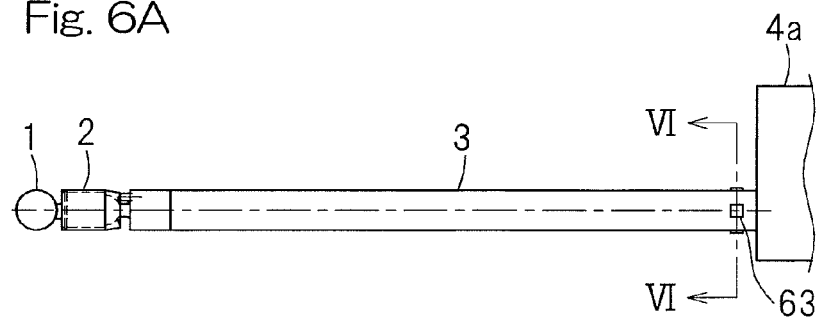
FIG. 6A is a fragmentary diagram illustrating the remote controlled actuator, showing another example of a cutting force estimator.
Figure 6B:
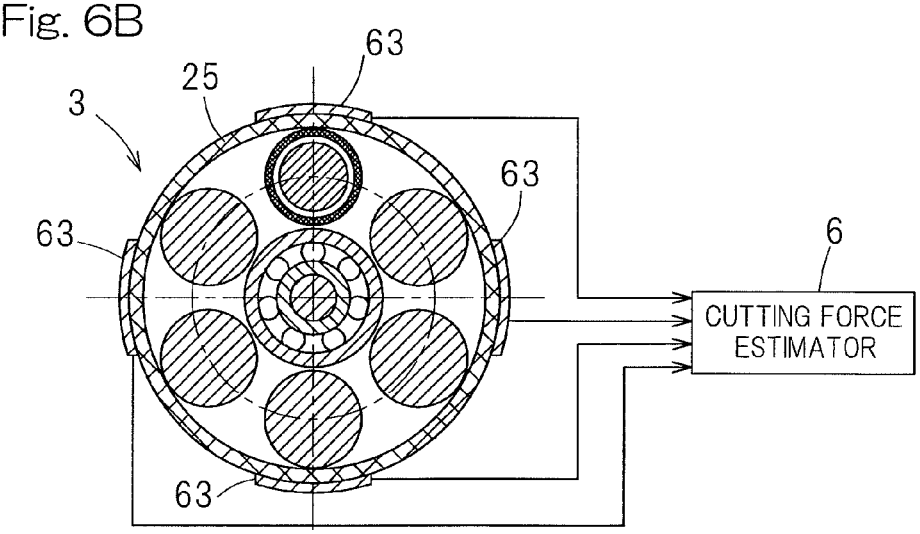
FIG. 6B is a cross sectional view taken along the line VI-VI in FIG. 6A.

FIGS. 6A and 6B illustrate another example of the cutting force estimator 6. As best shown in FIG. 6B, a flexure amount measuring section 63 for measuring the amount of flexure of the spindle guide section 3 is employed, and the cutting force estimator 6 estimates mainly the magnitude of the radial force Fr (FIGS. 4A and 4B) in the cutting force from the amount of flexure measured by the flexure amount measuring section 63. When the radial force Fr acts on the work to be processed through the tool 1, the spindle guide section 3 undergoes flexure, and therefore, measurement of the amount of flexure of the spindle guide section 3 with the flexure amount measuring section 63 makes it possible to estimate the magnitude of the radial force Fr.

In the case of FIGS. 6A and 6B, the flexure amount measuring section 63 is a strain sensor and is pasted to four locations of a root portion outer peripheral surface of the outer shell pipe 25 of the spindle guide section 3 in a fashion spaced an equal distance from each other in the circumferential direction. Since the strain in the outer shell pipe 25 is maximum at a root portion, it is recommended to paste the strain sensor to the root portion of the outer shell pipe 25. Where the flexure amount measuring section 63 is employed in the form of the strain sensor, when the radial force Fr acts on the work W to be processed through the tool 1, a detection signal of the strain sensor situated on a peripheral surface of the spindle guide section 3 varies in a compressive direction or in a tensile direction depending on the direction of flexure, and therefore, the magnitude of the radial force Fr can be estimated. Also, when the feed force Pf (FIGS. 4A and 4B) acts on the work W to be processed through the tool 1, the strain sensor situated at any circumferential position on the peripheral surface of the outer shell pipe 25 changes in the compressive direction, and therefore, the magnitude of the feed force Pf can also be estimated.

Where the ratio of the respective magnitudes of the principle force Fc, the radial force Fr and the feed force Pf is fixed, the magnitudes of the principle force Fc and the feed force Pf can be estimated if the magnitude of the radial force Fr is determined. On the other hand, where the ratio of the respective magnitudes of those forces changes, it is recommended to concurrently use a cutting force estimator 6 for estimating the respective magnitudes of the forces Fc and Pf.

Figure 7A:
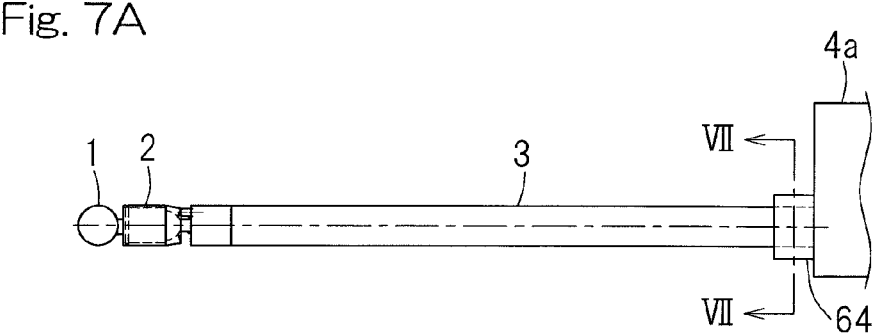
FIG. 7A is a fragmentary diagram illustrating the remote controlled actuator, showing a different example of the cutting force estimator.
Figure 7B:
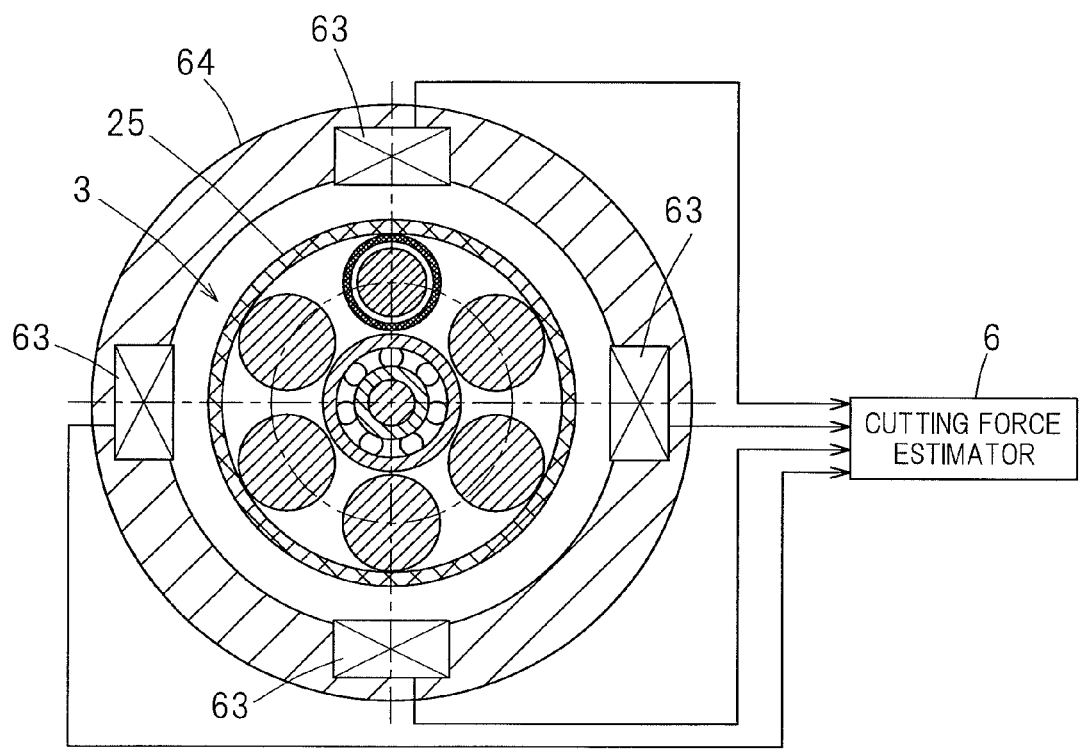
FIG. 7B is a cross sectional view taken along the line VII-VII in FIG. 7A.

As shown in FIGS. 7A and 7B, the flexure amount measuring section 63 may be a displacement sensor for measuring a displacement of the spindle guide section 3 at an arbitrarily chosen location. Even in such case, as is the case with the description made above, the magnitude of the radial force Fr can be estimated by the cutting force estimator 6. In the example shown in FIGS. 7A and 7B, a cylindrical sensor housing 64 is provided on an outer periphery of the root portion of the spindle guide section 3 as shown in FIG. 7A and the flexure amount measuring section 63 comprised of an optical displacement sensor is provided at four locations on an inner periphery of the sensor housing 64 in a fashion spaced an equal distance from each other in the circumferential direction as shown in FIG. 7B. By the flexure amount measuring section 63, the displacement of the outer shell pipe 25 of the spindle guide section 3 is measured.

Figure 8A:
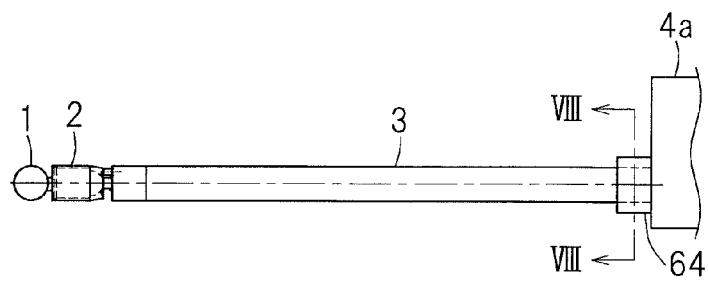
FIG. 8A is a fragmentary diagram illustrating the remote controlled actuator, showing a further different example of the cutting force estimator.
Figure 8B:
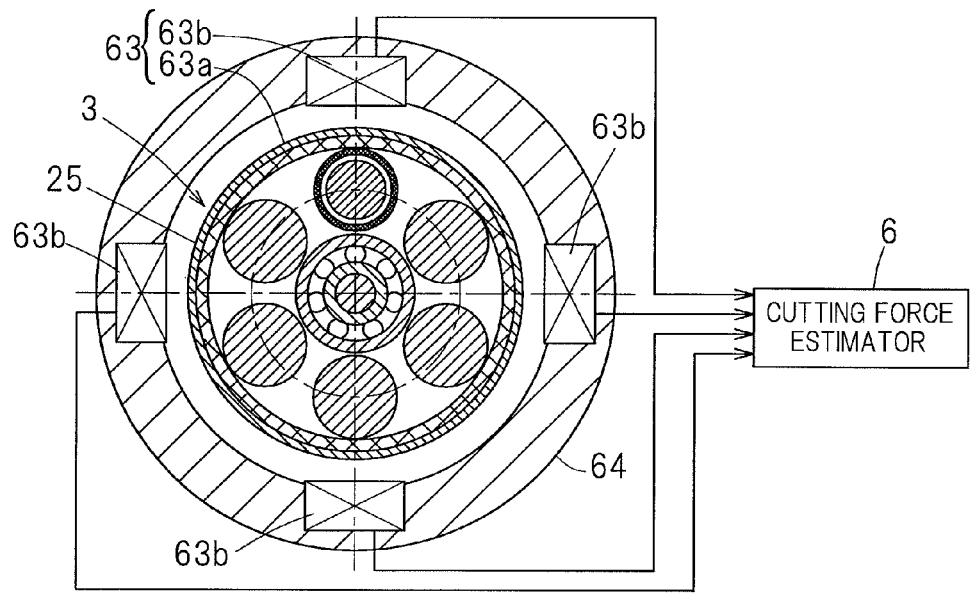
FIG. 8B is a cross sectional view taken along the line VIII-VIII in FIG. 8A.

As shown in FIGS. 8A and 8B, the flexure amount measuring section 63 may be comprised of a magnetic displacement sensor made up of an encoder 63a serving as a to-be-detected element and a Hall sensor 63b. The example shown in FIGS. 8A and 8B is such that the annular encoder 63a is mounted on the root portion of the outer shell pipe 25 of the spindle guide section 3 and the Hall sensor 63b is provided at four locations on the inner periphery of the sensor housing 64, as described in FIGS. 7A and 7B, in a fashion spaced an equal distance from each other in the circumferential direction. The number of the Hall sensors 63b is not specifically limited. By means of this flexure amount measuring section 63, the displacement of the outer shell pipe 25 of the spindle guide section 3 is measured.

It is to be noted that the flexure amount measuring section 63 referred to above may be comprised of an eddy current displacement sensor.

Figure 9:
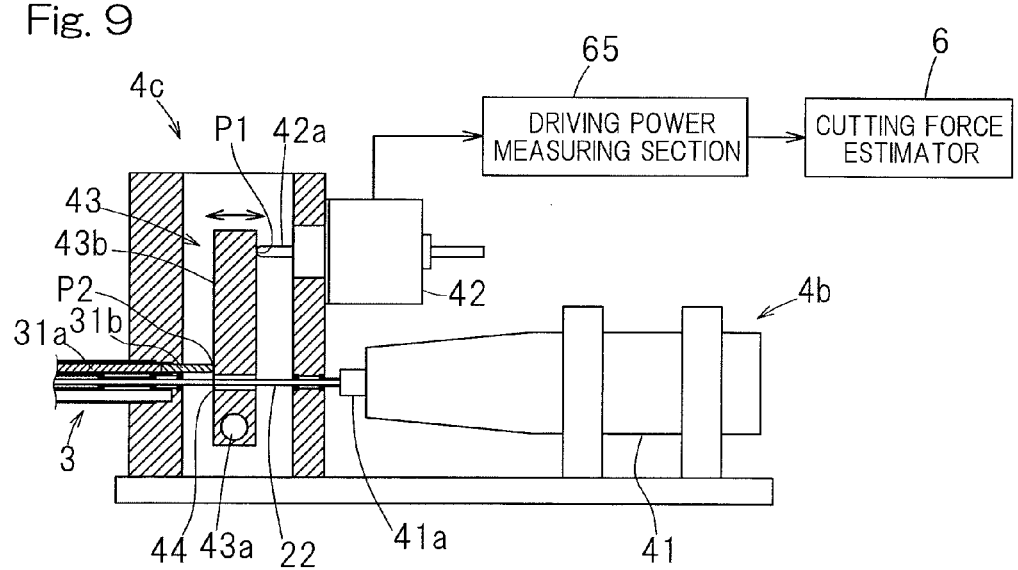
FIG. 9 is a sectional view illustrating the tool rotation drive mechanism and the attitude alteration drive mechanism, showing a still further different example of the cutting force estimator.

FIG. 9 illustrates a different example of the cutting force estimator 6. In this example, the use is made of a driving power measuring section 65 for measuring a driving power of the attitude altering drive source 42, and the cutting force estimator 6 estimates mainly the magnitude of the radial force Fr in the cutting force from the driving power measured by the driving power measuring section 65. For the driving power measuring section 65, the supply power meter 47 (FIGS. 3A and 3B) for detecting the amount of the electric power supplied to the attitude altering drive source 42 may be utilized.

When the radial force Fr acts through the tool 1 on the work to be processed, such a force is transmitted to the attitude altering drive source 42 through the attitude altering member 31 so that the driving power of the attitude altering drive source 42 selectively increases or decreases, and therefore, the magnitude of the radial force Fr can be estimated when the driving power is measured by the driving power measuring section 65.

Figure 10A:
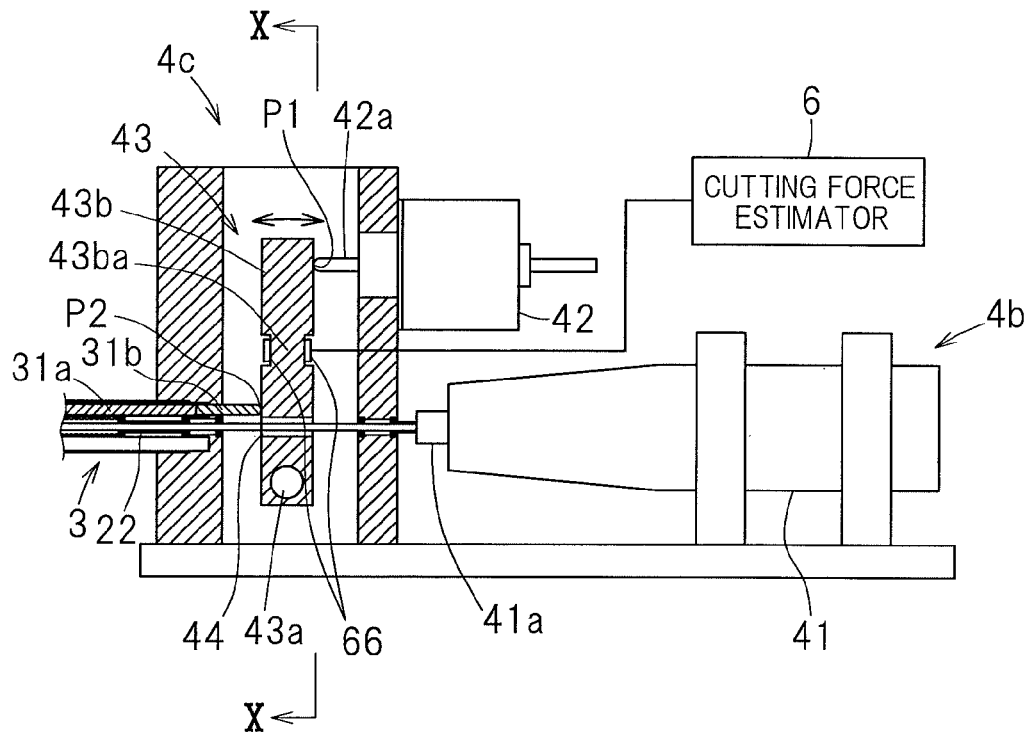
FIG. 10A is a sectional view illustrating the tool rotation drive mechanism and the attitude alteration drive mechanism, showing a still further different example of the cutting force estimator.
Figure 10B:
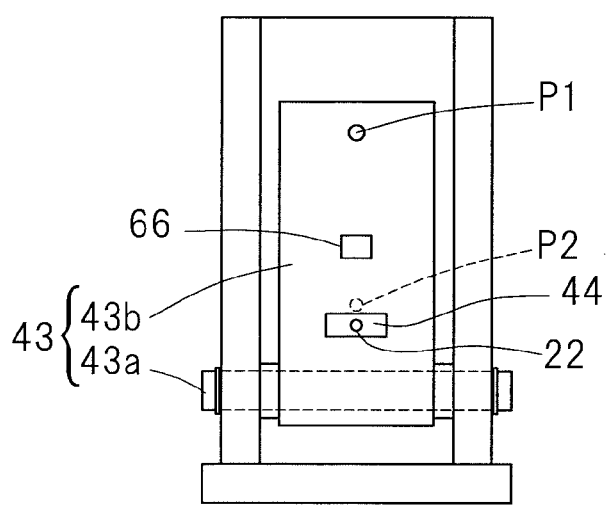
FIG. 10B is a cross sectional view taken along the line X-X in FIG. 10A.

A further different example of the cutting force estimator 6 is shown in FIGS. 10A and 10B. In this example, a strain sensor 66 is provided as a strain detector for detecting a strain occurring in the lever mechanism 43 for transmitting the driving power of the attitude altering drive source 42 to the attitude altering member 31, and the cutting force estimator 6 estimates mainly the magnitude of the radial force Fr in the cutting force from a detection value of the strain sensor 66. As shown in FIG. 10A, the strain sensor 66 in the illustrated example is of a structure, in which a thin walled strain inducing element 43ba is integrally formed at an intermediate portion of the lever 43b of the lever mechanism 43 and strain sensor 66 for detecting strains, which may be generated in the strain inducing element 43ba, are fixed to front and rear surfaces of the strain inducing element 43ba.

When the radial force Fr acts through the tool 1 on the work to be processed, such force is transmitted to the lever mechanism 43 through the attitude altering member 31 so that the strain is induced in the lever 43b of the lever mechanism 43, and therefore, the magnitude of the radial force Fr can be estimated when such strain is detected by the strain sensor 66.

FIGS. 11A and 11B illustrate a second preferred embodiment of the present invention. The remote controlled actuator according to this second embodiment is of a design, in which the two guide pipes 30 are provided at the peripheral positions spaced 180° in phase from each other within the outer shell pipe 25 and the attitude altering member 31 is reciprocally movably inserted within guide holes 30a, which are inner diametric holes of the guide pipes 30. Between those two guide pipes 30, a plurality of reinforcement shafts 34 are arranged on the same pitch circle as that of the guide pipes 30. No restoring elastic member 32 is provided. The guide faces F1 and F2 are spherical surfaces each having the center of curvature lying at the point O or cylindrical surfaces each having a lateral X-axis as a longitudinal axis passing through the point O.

The drive unit 4 (not shown in FIG. 11A or 11B) is provided with two attitude altering drive sources 42 (not shown in FIG. 11A or 11B) for selectively advancing and retracting respective attitude altering members 31 so that when those two attitude altering drive sources 42 are driven in respective directions opposite to each other, the distal end member 2 can be altered in attitude.

By way of example, when the upper attitude altering member 31 shown in FIGS. 11A and 11B is advanced towards the tip end side and the lower attitude altering member 31 is retracted, the housing 11 for the distal end member 2 is pressed by the upper attitude altering member 31 and, therefore, the distal end member 2 is altered in attitude along the guide surfaces F1 and F2 with the tip end side oriented downwards as viewed in FIG. 11A. Conversely, when both of the attitude altering members 31 are driven in the directions opposite thereto, the lower attitude altering member 31 urges the housing 11 for the distal end member 2 to allow the distal end member 2 to alter in attitude along the guide surfaces F1 and F2 with the distal end side oriented upwardly as viewed in FIG. 11A. At this time, the pressures from the upper and lower attitude altering members 31 and a reactive force from the constraint member 21 act on the distal end member connecting unit 15 and, accordingly, the attitude of the distal end member 2 is determined in dependence on the balance of those working forces.

According to this construction, since the housing 11 for the distal end member 2 is pressed by the two attitude altering members 31, as compared with the previously described embodiment in which it is pressed by the only attitude altering member 31, the attitude stability of the distal end member 2 can be increased.

FIGS. 12A and 12B illustrate a third preferred embodiment of the present invention. The remote controlled actuator according to this third embodiment makes use of three guide pipes 30 disposed within the outer shell pipe 25 and positioned at respective circumferential position spaced 120° in phase from each other within the outer shell pipe 25 and, correspondingly, three attitude altering members 31 accommodated within respective guide holes 30a, which are inner diametric holes of those guide pipes 30, for reciprocal movement relative to the associated guide pipes 30. Between the three guide pipes 30, a plurality of reinforcement shafts 34 are arranged on the same pitch circle as that of the guide pipes 30. No restoring elastic member 32 is provided. The guide surfaces F1 and F2 represents spherical surface having respective centers of curvature lying at the point O and the distal end member 2 can be tilted in any desired direction.

The drive unit 4 is provided with three attitude altering drive sources 42 (42U, 42L and 42R) (FIG. 13) for reciprocally operating respective attitude altering members 31 (31U, 31L and 31R), and those attitude altering drive sources 42 cooperate with each other to drive the distal end member 2 to alter the attitude thereof.

By way of example, when one of the attitude altering members 31U, which is shown in an upper side of FIGS. 12A and 12B, is advanced towards the tip end side while the other two attitude altering members 31L and 31R are retracted, the housing 11 for the distal end member 2 is pressed by the attitude altering member 31U shown in the upper side of FIGS. 12A and 12B to allow the distal end member 2 to be altered in attitude along the guide surfaces F1 and F2 with the tip end side consequently oriented downwardly as viewed in FIG. 12A. At this time, those attitude altering drive sources 42 are controlled so that the amount of advance or retraction of each of the attitude altering members 31 may become proper. On the other hand, when each of those attitude altering members 31 is conversely retracted or advanced, the housing 11 for the distal end member 2 is pressed by the attitude altering members 31L and 31R, which are shown on lower left and lower right sides, and, consequently, the distal end member 2 is altered in attitude along the guide surfaces F1 and F2 with the tip end side oriented upwardly as viewed in FIG. 12A.

Also, when while the attitude altering member 31U on the upper side is held still, the attitude altering member 31L on the left side is advanced towards the tip end side and the attitude altering member 31R on the right side is retracted, the housing 11 for the distal end member 2 is pressed by the attitude altering member 31L on the left side to allow the distal end member 2 to be oriented rightwards, that is, to be altered in attitude along the guide surfaces F1 and F2 with the distal end member 2 oriented towards a rear side of the sheet of the drawing of FIG. 12A. Conversely, when the attitude altering members 31L and 31R on the left and right sides are advanced and retracted, the housing 11 for the distal end member 2 is pressed by the attitude altering member 31R on the right side, allowing the distal end member 2 to be altered in attitude so that the distal end member 2 can be guided along the guide surfaces F1 and F2 so as to be oriented leftwards.

Figure 13:
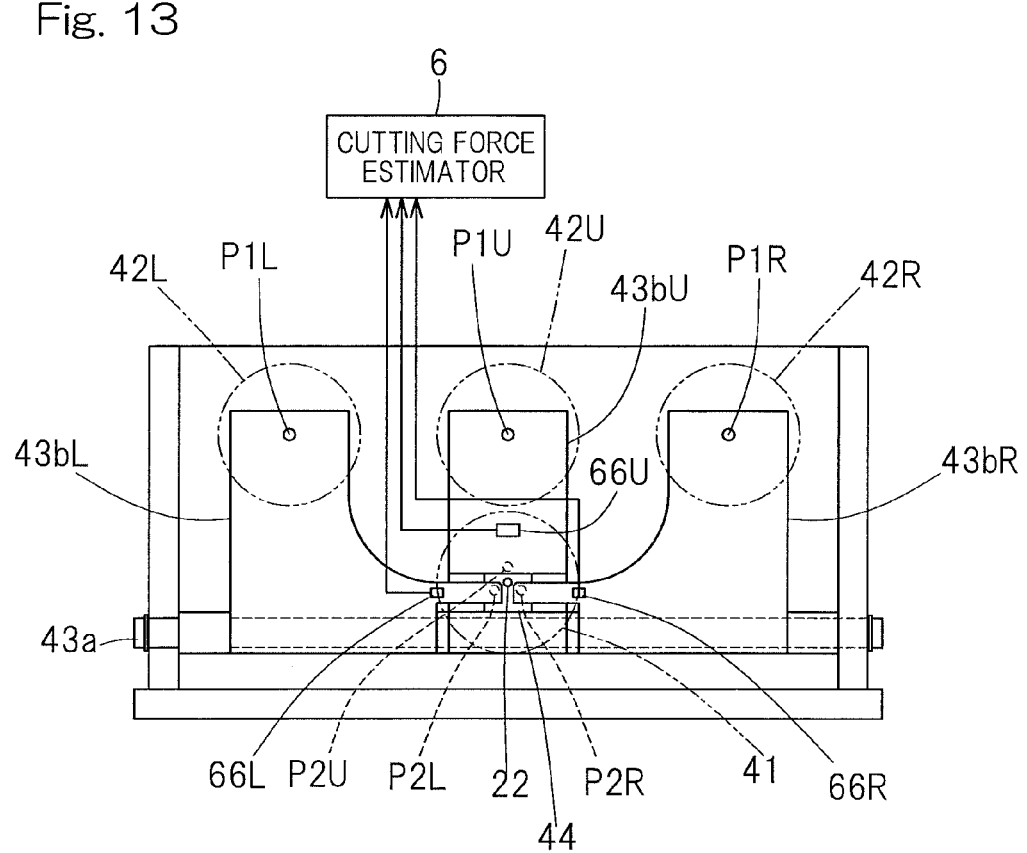
FIG. 13 is a diagram illustrating a front elevational view of the tool rotation drive mechanism and the attitude alteration drive mechanism, shown together with the control system.

The use of the attitude altering members 31 at the three circumferential locations as hereinabove described is effective to allow the distal end member 2 to be altered in attitude in two axis directions (X-axis and Y-axis directions) upwardly or downwardly and leftwards or rightwards. At this time, respective pressures from the three attitude altering members 31 and the reactive force from the constraint member 21 act on the distal end member connecting unit 15 and, therefore, the attitude of the distal end member 2 is determined in dependence on the balance of those working forces. According to the above described construction, since the housing 11 for the distal end member 2 is pressed by the three attitude altering members 31, the attitude stability of the distal end member 2 can be further increased. It is, however, to be noted that if the number of the attitude altering members 31 used is increased, the attitude stability of the distal end member 2 can be still further increased.

Where the attitude altering members 31 are provided at the three circumferential locations, the attitude altering drive mechanism 4c may be constructed, for example, such as shown in FIG. 13. In other words, the attitude altering drive mechanism 4c is so constructed that the three attitude altering drive sources 42 (42U, 42L and 42R) for selectively advancing and retracting the attitude altering members 31 (31U, 31L and 31R) may be arranged along a leftward and rightward direction and parallel to each other. Levers 43b (43bU, 43bL and 43bR) corresponding to the attitude altering drive sources 42 may be provided for pivotal movement about a common support pin 43a to enable the force of the output rod 42a (FIG. 3) of each of the attitude altering drive sources 42 to work on the point P1 (P1U, P1L and P1R) of the respective lever 43b, which is spaced a long distance from the support pin 43a, and to enable the force to work on the attitude altering member 31 at the point P2 (P2U, P2L and P2R), which is spaced a short distance from the support pin 43a. Accordingly, the output of each of the attitude altering drive sources 42 can be increased and then transmitted to the corresponding attitude altering member 31. It is to be noted that the rotary shaft 22 is passed through an opening 44 defined in the lever 43bU for the attitude altering member 31U on the upper side.

Also, where the strain sensors 66 as a strain detector for detecting the strain appearing in the lever mechanism 43 is employed, strain sensors 66U, 66L and 66R as a strain detector for detecting the strain generated in the corresponding lever 43b are pasted to the respective levers 43 (43bU, 43bL and 43bR). The cutting force estimator 6 estimates the magnitude of mainly the radical force Fr in the cutting force from a detection value of each of those strain sensors 66.

FIGS. 14A to 14C illustrate a fourth preferred embodiment of the present invention. In this fourth embodiment, a radially extending groove portion 11c (as best shown in FIG. 14C) is formed in the base end face of the housing 11 for the distal end member 2 and the attitude altering member 31 has its end held in contact with a bottom of this groove portion 11c. The groove portion 11c and the attitude altering member 31 cooperate with each other to define a rotation preventive mechanism 37 that is operable to prevent the distal end member 2 from rotating about the center line CL of the distal end member 2 relative to the spindle guide member 3 when the tip end portion of the attitude altering member 31 inserted into the groove portion 11c is held in abutment with a side face of the groove portion 11c.

According to the rotation preventive mechanism 37 in the manner as hereinabove described, even when the distal end member 2 then holding the tool 1 becomes uncontrollable as a result of any trouble occurring in the attitude altering drive mechanism 4c for controlling the selective advance and retraction of the attitude altering member 31 and/or the control device therefor, it is possible to avoid the possibility that the site to be processed may be impaired as a result of rotation of the distal end member 2 about the center line CL or the distal end member 2 itself is broken.

Although the forgoing fourth embodiment of the present invention makes use of the attitude altering member 31 at one location in the circumferential direction, it can be equally applicable to the structure, in which the attitude altering member 31 is provided at two locations spaced 180° in phase from each other in the circumferential direction or at three locations spaced 120° in phase from each other in the circumferential direction.

FIGS. 15A and 15B illustrate a fifth preferred embodiment of the present invention. The remote controlled actuator according to this fifth embodiment is featured in that the spindle guide section 3 is of a structure in which a hollow 24 of the outer shell pipe 25 is defined by a round hole portion 24a at the center thereof and three grooved portions 24b radially outwardly recessed from respective circumferential positions on an outer periphery of the round hole portion 24a, which are spaced 120° in phase from each other. A peripheral wall at a tip of each of the grooved portions 24b represents a semicircular sectioned configuration. The rotary shaft 22 and the rolling bearings 26, both referred to previously, are accommodated within the round hole portion 24a and the attitude altering member 31 is accommodated within each of the grooved portions 24b.

With the outer shell pipe 25 so designed as to have the above described sectional shape, the wall thickness t of the outer shell pipe 25 excluding those portions thereof where the grooved portions 24b are formed is increased and, hence, the geometric moment of inertia of area of the outer shell pipe 25 is increased. In other words, the rigidity of the spindle guide section 3 is increased. Thereby, not only can the positioning accuracy of the distal end member 2 be increased, but also the cutting ability can be increased. Also, since the guide pipes 30 are arranged in the respective grooved portions 24b, positioning of the guide pipes 30 in the circumferential direction can be easily accomplished and a good assemblability can be appreciated.

Although the fifth embodiment described above is the example, in which the attitude altering member 31 is provided at the three circumferential locations spaced 120° in phase from each other, it can be equally applicable to the structure, in which the attitude altering member 31 is provided at two locations spaced 180° in phase from each other in the circumferential direction, or the structure in which a combination of the attitude altering member 31, provided at one location, with the corresponding restoring elastic member 32 is employed. By way of example, in the structure in which the attitude altering member 31 is provided at one location in the circumferential direction, the grooved portion 24b in the hollow 24 may be provided at three locations in the circumferential direction as is the case with the outer shell pipe 25 shown in and described with reference to FIGS. 15A and 15B, and, at the same time, the attitude altering member 31 may be accommodated within one of the grooved portions 24b while the reinforcement shafts 24 (See, for example, FIGS. 2A to 2C) are accommodated within the remaining grooved portions 24b.

Figure 16:
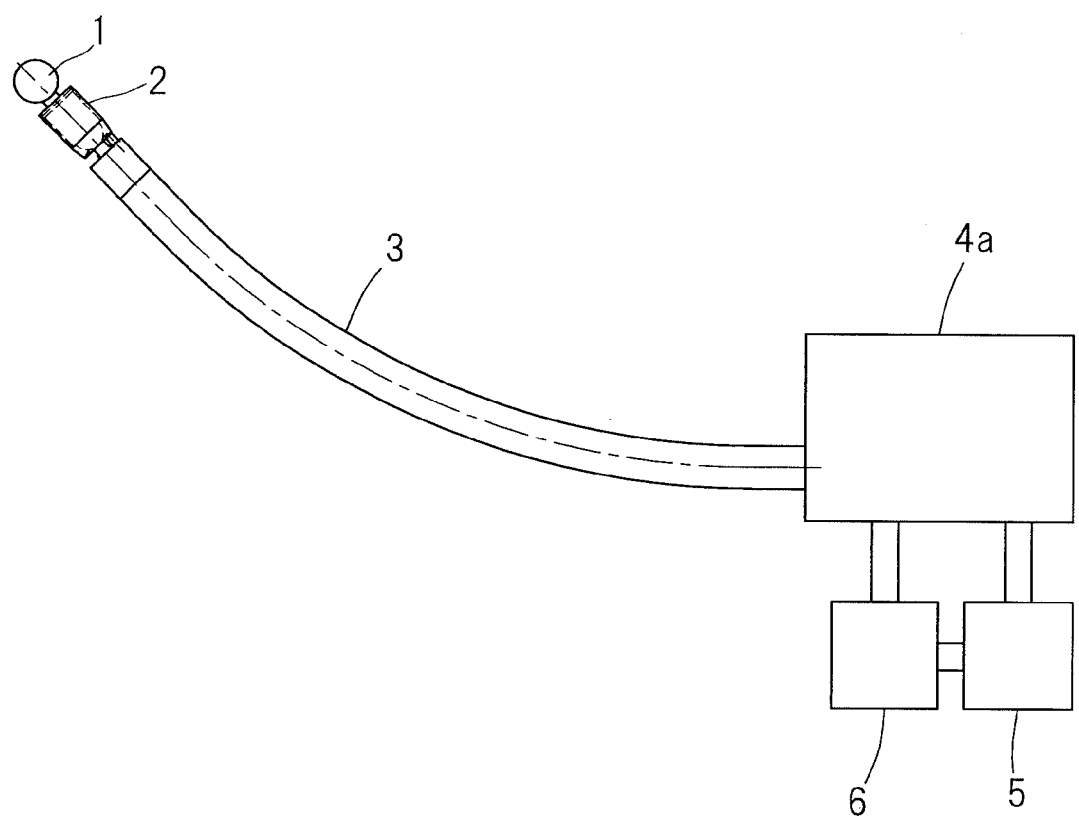
FIG. 16 is a diagram showing a schematic construction of the remote controlled actuator employing the spindle guide section of a different shape.

While in any one of the foregoing embodiments the spindle guide section 3 has been shown and described as extending straight, since the remote controlled actuator of the present invention is such that the attitude altering member 31 has a flexibility and, even when the spindle guide section 3 is curved, the attitude alteration of the distal end member 2 takes place assuredly, the spindle guide section may have a curved shape in an initial condition as shown in FIG. 16. Alternatively, only a portion of the spindle guide section 3 may have a curved shape. If the spindle guide section 3 has a curved shape, it may happen that insertion of the distal end member 2 deep into the bore, where the spindle guide section of the straight shape fails to reach, can be accomplished, and, therefore, the processing of the opening for insertion of the artificial joint prior to a surgery being performed to replace with the artificial joint can be formed precisely and accurately.

Where the spindle guide section 3 is designed to represent the curved shape, the outer shell pipe 25, the guide pipes 30 and the reinforcement shafts 34 need be curved in shape. Also, an easily deformable material is preferably used for the rotary shaft 22 and a shape memory alloy, for example, can be suitably employed therefor. Other than the wire 31a, the attitude altering member 31 may be comprised of a plurality of balls or a plurality of pillar shaped elements so curved as to follow the curvature of the guide pipes 30. In the latter case, the pillar shaped element so curved is preferably of a shape short in length and having corners chamfered.

Figure 17:
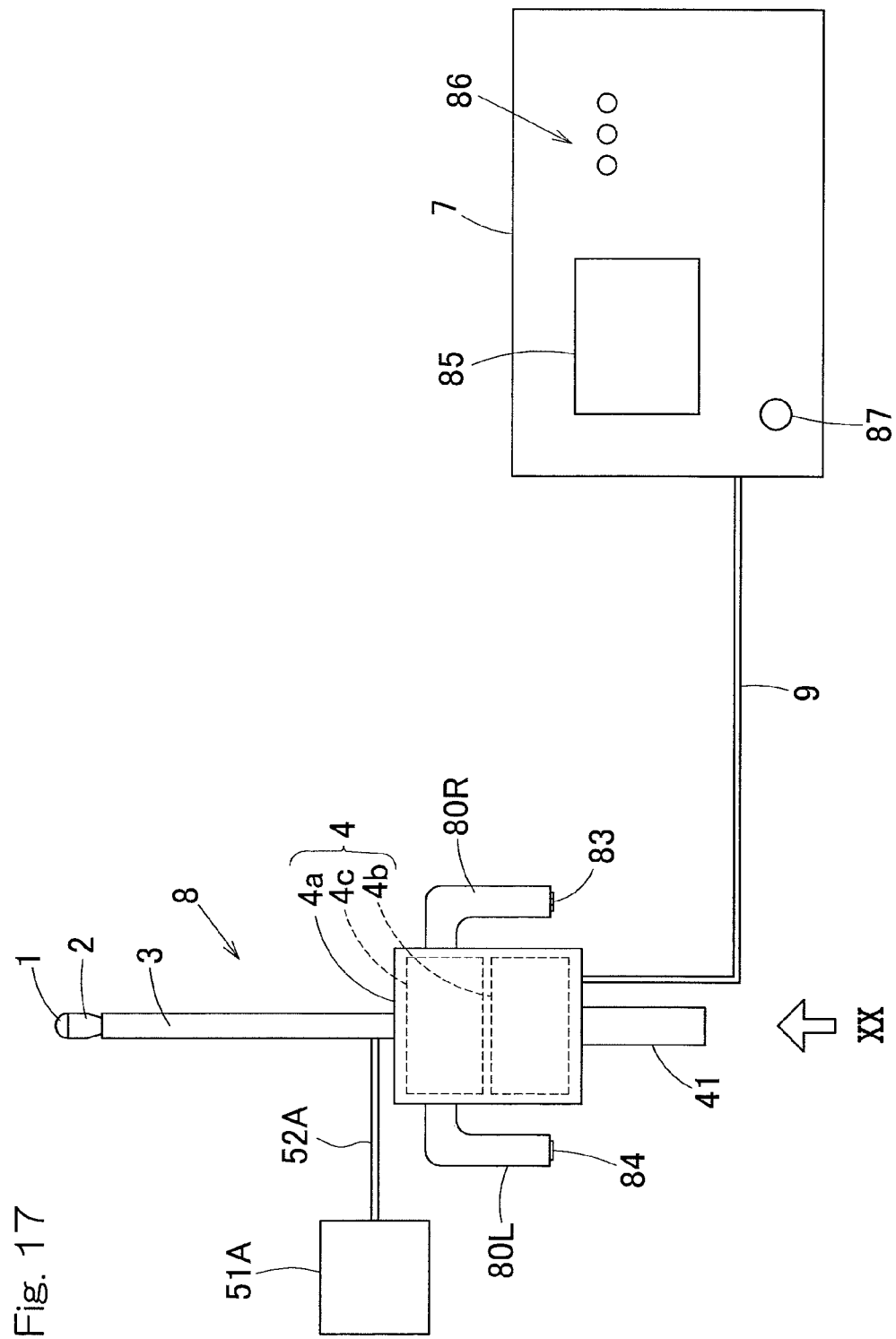
FIG. 17 is a diagram showing a schematic construction of the remote controlled actuator according to a sixth preferred embodiment of the present invention.
Figure 18:
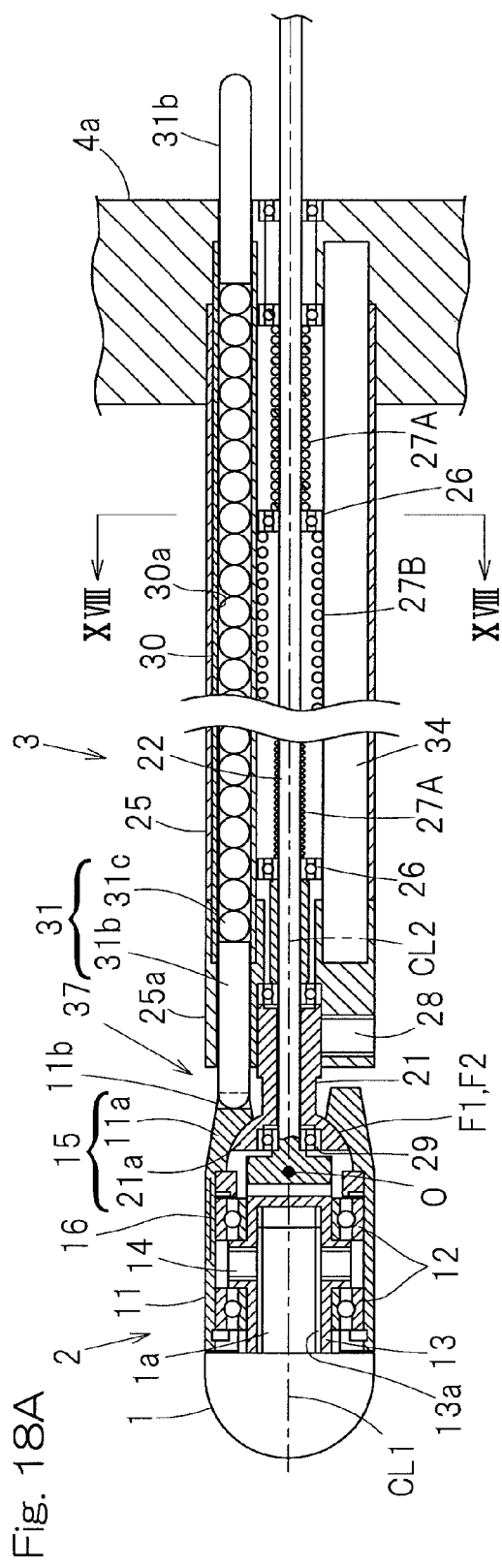
FIG. 18A is a sectional view showing the distal end member and the spindle guide section both employed in the remote controlled actuator.
FIG. 18B is a cross sectional view taken along the line XVIII-XVIII in FIG. 18A.
FIG. 18C is a diagram showing the connecting unit between the distal end member and the rotary shaft.
FIG. 18D is a view showing the housing for the distal end member as viewed from the base end side.
Figure 19:
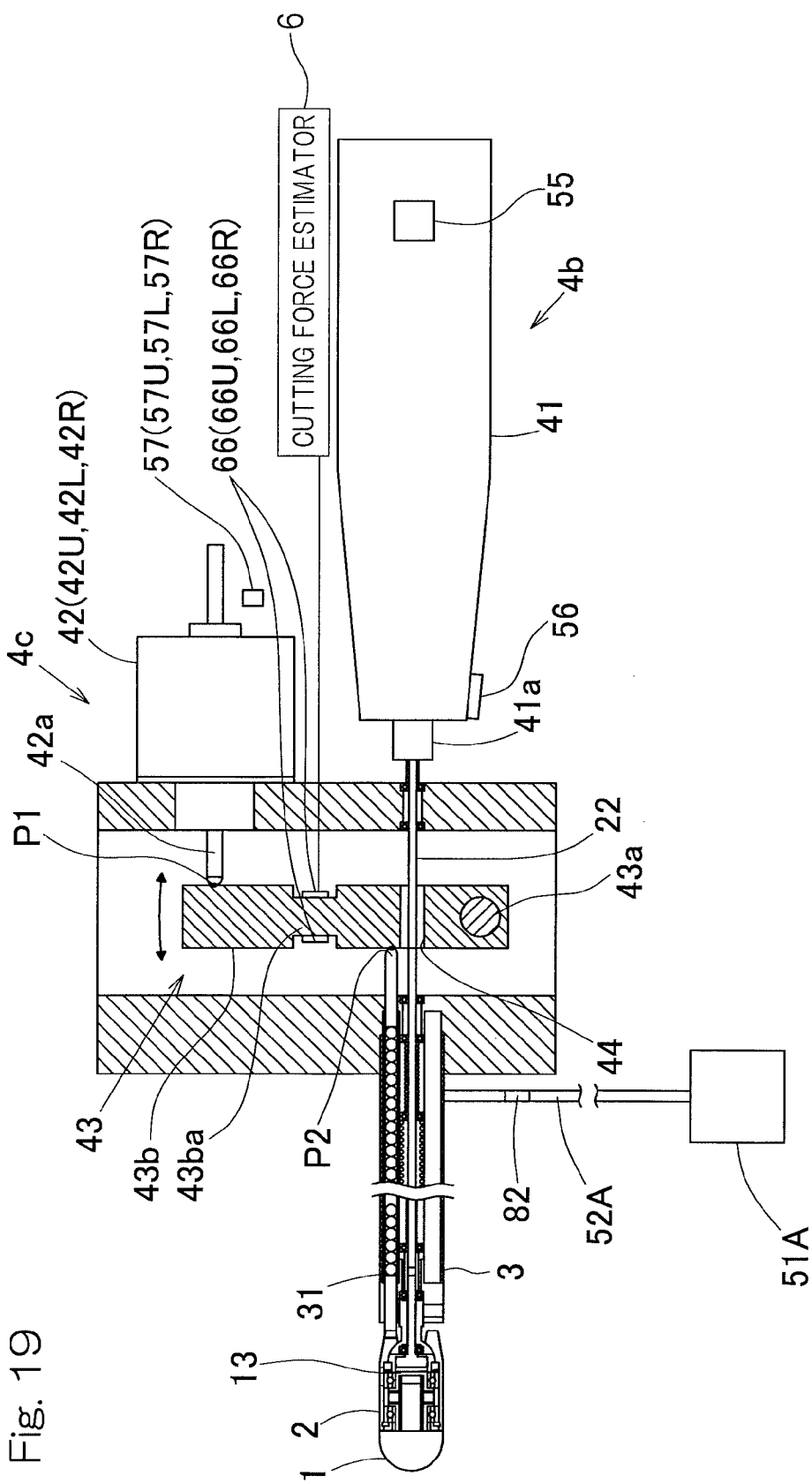
FIG. 19 is a sectional view showing the structure mainly within a drive unit housing of the remote controlled actuator.

A sixth preferred embodiment of the present invention will now be described in detail with particular reference to FIGS. 17 to 24. In the drawings referred to in the description that follows, component parts identical with or similar to those employed in the embodiment referred to in the foregoing description are designated by like reference numerals and the details thereof are therefore not reiterated. FIG. 17 illustrates a schematic construction of the remote controlled actuator according to this sixth embodiment of the present invention. In this sixth embodiment, in addition to the cutting force estimator 6 of the type which is an essential requirement in the remote controlled actuator according to the practice of the previously described first embodiment, abnormality detector 16, 55, 56, 57, 66 and 82 as will be described in detail later are employed. The cutting force estimator 6 employed in the practice of this sixth embodiment estimates the magnitude of the radial force Fr in the cutting force by detecting, with the strain sensor (strain detector) 66, the strain induced in the lever 43b of the lever mechanism 43 such as shown in FIGS. 10A and 10B in connection with the previously described first embodiment (FIG. 19).

Referring to FIG. 17, the remote controlled actuator shown therein includes an actuator body 8, a control box 7, which is a controller connected with the actuator body 8 through an electric cable 9, and a liquid lubricant supply device 51A for supplying a liquid lubricant to the actuator body 8. The actuator body 8 has its structure basically similar to that described in connection with the first embodiment.

FIGS. 18A to 18D correspond to FIGS. 12A and 12B showing the previously described third embodiment and, therefore, component parts identical with or similar to those shown in FIGS. 12A and 12B are designated by like reference numerals with the details thereof being not reiterated. In FIGS. 18A to 18D, the housing 11 for the distal end member 2 is provided with a temperature sensor 16 as a temperature detector which serves as an abnormality detector for detecting the temperature of the housing 11. Also, of the wire 31a and the pillar shaped pins 31b, which is/are used to form the attitude altering member 31 employed in the practice of the previously described third embodiment, balls 31c are employed in place of the wire 31a.

Even in this sixth embodiment, a rotation preventive mechanism 37 of a structure similar to that employed in the practice of the previously described fourth embodiment (as best shown in FIGS. 14A to 14C) is employed and, accordingly, prevention of the distal end member 2 from rotating can be accomplished at a required time.

As best shown in FIG. 19, the tool rotation drive mechanism 4b includes a tool rotation drive source 41. This tool rotation drive source 41 is, for example, an electrically driven motor having its output shaft 41a coupled with the base end of the rotary shaft 22. The rotary shaft 22 extends through an opening 44 defined in the lever 43 as will be detailed later. The number of revolutions of the tool rotation drive source 41 is detected by a rotational speed sensor 55. This rotational speed sensor 55 forms a rotation detector for detecting the number of revolutions of the spindle 13. Also, the tool rotation drive source 41 has a vibration sensor 56 fitted thereto for detecting the magnitude of vibration occurring in the tool rotation drive source 41. This vibration sensor 56 forms a vibration detector for detecting the magnitude of vibration occurring in the spindle 13.

The attitude altering drive mechanism 4c referred to above includes three attitude control drive sources 42 (42U, 42L and 42R) corresponding respectively to the attitude altering members 31 (31U, 31L and 31R). The attitude control drive sources 42 are employed in the form of, for example, electrically driven linear actuators and movement of an output rod 42a thereof movable leftwards and rightwards as viewed in FIG. 19 is transmitted to the attitude altering member 31 through a lever mechanism 43 interposed between the attitude altering drive source 41 and the attitude altering member 31. The position of selective advance or retraction of the output rod 42a, that is, the position of activation of each of the attitude control drive sources 42, is detected respectively by an encoder 57 (57U, 57L and 57R). Those encoders 57 form a locked state detector for detecting whether or not the attitude of the distal end member 2 is locked.

The lever mechanism 43 includes a pivot lever 43b pivotable about a support pin 43a and is so designed and so configured as to allow a force of the output rod 42a to work on a working point P1 of the lever 43b, which is spaced a long distance from the support pin 43a, and as to apply a force to the attitude altering member 31 at a force point P2, which is spaced a short distance from the support axis 43a, wherefore an output of the attitude altering drive source 42 can be increased and then transmitted to the attitude altering member 31. As is the case with FIG. 13 pertaining to the previously described first embodiment, the strain sensor 66, in which the thin walled strain inducing element 43ba is integrally formed at an intermediate portion of the lever 43b and the strain sensors 66U, 66L and 66R for detecting strains, which may be generated in the strain inducing element 43ba, are fixed to front and rear surfaces of the strain inducing element 43ba. Those strain sensors 66 is not only used in the cutting force estimator 6, but forms the locked state detector for detecting whether or not that the attitude of the distal end member 2 is locked and is used as a working force detector for detecting the magnitude of the force acting on the distal end member 2.

Figure 20:
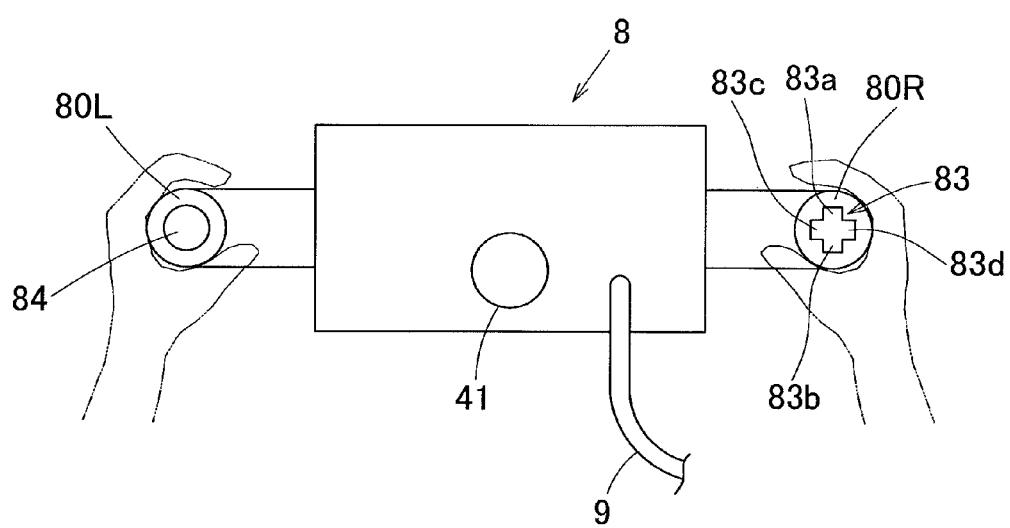
FIG. 20 is a diagram as viewed in a direction along the arrow XX in FIG. 17.

As shown in FIGS. 17 and 20, left and right side faces of the drive unit housing 4a is provided with a pair of left and right handles 80L and 80R. The left handle 80L has a tip end provided with a rotation ON/OFF operating piece 84, or a rotation operating section, for selectively rotating or halting the spindle 13. The rotation ON/OFF operating piece 84 is, for example, in the form of a push button switch. The right handle 80R has its tip end provided with the attitude altering operation piece 83 for altering the attitude of the distal end member 2. The attitude altering operation piece 83 is, for example, a crisscross switch having four operating pieces 83a to 83d arranged in a cross form and those four operating pieces 83a to 83d are represented respectively by an upper tilt operating piece 83a for tilting the distal end member 2 so as to be oriented upwardly, a lower tilt operating area 83b for tilting it so as to be oriented downwardly, a left tilt operating piece 83c for tilting it so as to be oriented leftwards, and a right tilt operating piece 83d for tilting it so as to be oriented rightwards. As shown by the double dotted chain line in FIG. 20, the actuator body 8 can be held with the handles 80L and 80R gripped by opposite hands. In this condition, the rotation ON/OFF operating piece 84 can be manipulated by a left hand then gripping the left handle 80L and the attitude altering operation piece 83 can be each manipulated by the right hand then gripping the right handle 80R.

The control box 7 referred to previously has a computer 70 (best shown in FIG. 21) built therein, which operates to perform various controls. Those various controls will be discussed in detail later. As best shown in FIG. 17, the control box 7 has an outer front surface provided with a display panel 85 of a liquid crystal display type, an indicator lamp 86, and an initial attitude operating piece 87. The initial attitude operating piece 87 is employed in the form of, for example, push button switches.

The liquid lubricant supply device 51A referred to hereinbefore is fluid connected with a portion in the vicinity of the base end of the spindle guide section 3 through a supply tube 52A, which is a liquid lubricant supply passage, in a manner similar to the liquid coolant supply device 51 shown in FIG. 5 and described in connection with the first embodiment. The liquid lubricant supplied from the liquid lubricant supply device 51A flows through the spindle guide section 3 and the interior of the distal end member 2 and is then discharged from the tip end of the distal end member 2 towards the tool 1. During this course of flow of the liquid lubricant, the rolling bearings 26 in the spindle guide section 3 and the rolling bearings 29 in the distal end member 2 are lubricated. Also, by the effect of the liquid lubricant discharged towards the tool 1, the tool 1 and the work to be cut are cooled. A portion of the supply tube 52A is provided with a pressure sensor 82, which forms an abnormality detector, for detecting the pressure of the liquid lubricant flowing through the supply tube 52A. This pressure sensor 82 is a liquid lubricant pressure detector for detecting the pressure of the liquid lubricant supplied within the spindle guide section 3.

Figure 21:
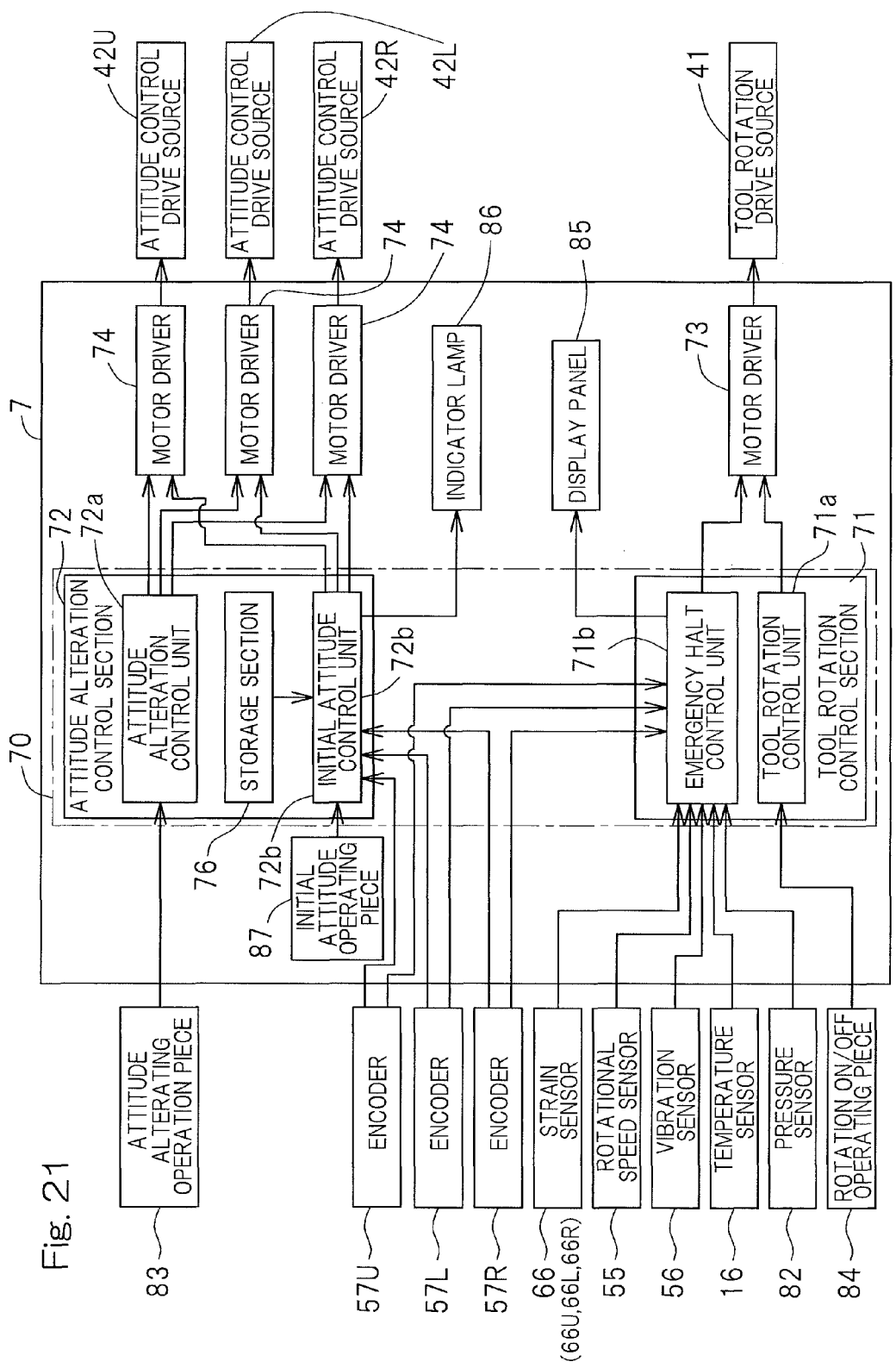
FIG. 21 is a block diagram showing the control system of the remote controlled actuator.

As shown in FIG. 21, the computer 70 within the control box 7 includes a tool rotation control section 71 for controlling the tool rotation drive source 41 and an attitude alteration control section 72 for controlling the attitude altering drive source 42 (42U, 42L and 42R).

The attitude alteration control section 72 is made up of an attitude alteration control unit 72a and an initial attitude control unit 72b.

The attitude alteration control unit 72a provides an output signal to a motor driver 74 in dependence on an actuation command signal resulting from an input manipulation of the attitude altering operation piece 83 to thereby drive the attitude control drive source 42 (42U, 42L and 42R). By way of example, the amount of drive of the attitude control drive source 42 is proportional to the operate time of the attitude altering operation piece 83. When depending on which one of the operating pieces 83a, 83b, 83c and 83d is manipulated, the direction of the output and the magnitude of the output for each of the attitude control drive sources 42U, 42L and 42R are changed, the attitude of the distal end member 2 can be altered.

For example, when the operating piece 83b is manipulated to provide an output signal, such output signal is provided to each of the attitude control drive sources 42U, 42L and 42R. Then, the upper attitude altering member 31U shown in FIGS. 18A to 18D is advanced towards the tip end side and the remaining two attitude altering members 31L and 31R are retracted. Once this takes place, the housing 11 for the distal end member 2 is pressed by the upper attitude altering member 31U with the distal end member 2 consequently altered in attitude along the guide faces F1 and F2 so as to permit the tip end side thereof to be oriented downwards in FIG. 18A. In the event that the operating piece 83a is manipulated to provide an output signal, each of the attitude altering members 31 is advanced or retracted in a direction reverse to that described above and the housing 11 for the distal end member 2 is pressed by the left and right attitude altering members 31L and 31R with the distal end member 2 consequently altered in attitude along the guide faces F1 and F2 so as to permit the tip end side to be oriented upwardly in FIG. 18A.

Also, in the event that the operating piece 83c is manipulated to provide an output signal, such output signal is provided to each of the left and right attitude control drive sources 42L and 42R to cause the right attitude altering member 31R to advance towards the tip end side and the left attitude altering member 31L to retract. Then, the housing 11 of the distal end member 2 is pressed by the right attitude altering member 31R and, consequently, the distal end member 2 is altered in attitude so as to be oriented leftwards, that is, towards the side forwardly of the plane of the sheet of FIG. 18A, along the guide faces F1 and F2. On the other hand, in the event that the operating piece 83d is manipulated to provide an output signal, the attitude altering members 31L and 31R are advanced or retracted in a manner reverse to those in the case of manipulating the operating piece 58c and the housing 11 of the distal end member 2 is therefore pressed by the left attitude altering member 31L, resulting in the attitude of the distal end member 2 altered so as to be oriented rightwards along the guide faces F1 and F2.

Since the attitude altering member 31 is provided at the three locations in the circumferential direction, the distal end member 2 can be altered in attitude in any of the two axis directions, upwards, downwards, leftwards and rightwards, in the manner as hereinabove described. The pressures from the three attitude altering members 31 and the reactive force from the detent member 21 act on the distal end member connecting unit 15 and the attitude of the distal end member 2 is determined depending on the balance of those working forces. Since the housing 11 for the distal end member 2 is pressed by those three attitude altering members 31, the attitude stability of the distal end member 2 is high.

Figure 22A:
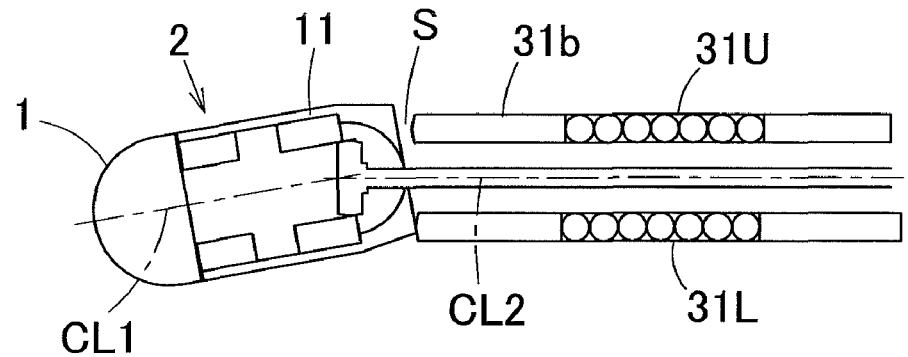
FIGS. 22A, 22B and 22C are explanatory diagrams showing different conditions of the distal end member and the spindle guide sections.
Figure 22B:
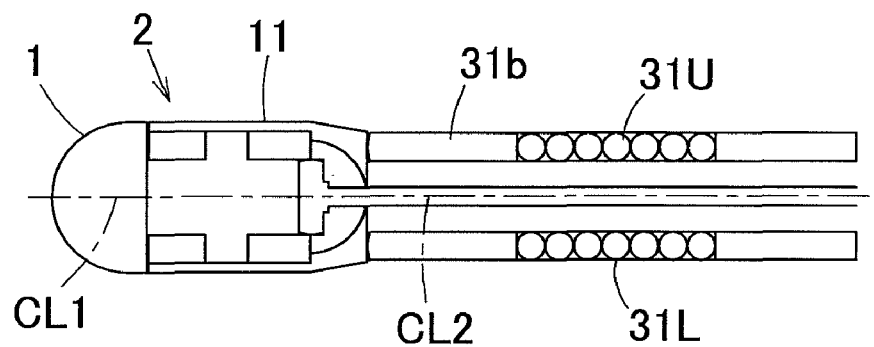
Figure 22C:
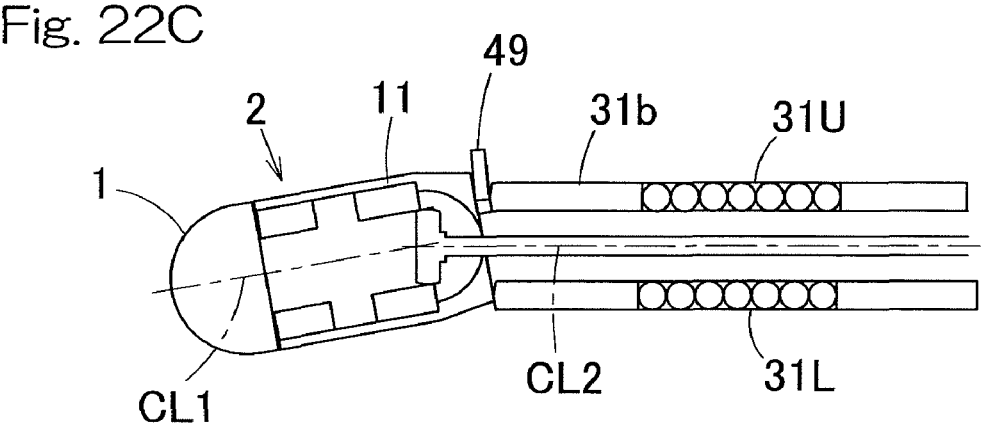

The initial attitude control unit 72b controls the distal end member 2 so as to assume a predetermined initial attitude through an actuation command signal outputted from the initial attitude operating piece 87. For example, immediately after the supply of an electric power to the remote controlled actuator is initiated or at the time of initial manipulation subsequent to replacement of the tool 1, there is the possibility that a gap S may be formed between the base end face of the housing 11 of the distal end member 2 and the pillar shaped pin 31b of the attitude altering member 31 as shown in FIG. 22A. For this reason, it is necessary to remove the gap S by allowing the distal end member 2 to resume the initial attitude. The initial attitude is the attitude, in which, for example, the center line CL1 of the distal end member 2 and the center line CL2 of the spindle guide section 3 are concentrically aligned with each other as shown in FIG. 22B. The actuation position of each of the attitude control drive sources 42 during the initial attitude is stored in a storage section 76. It is to be noted that FIGS. 22A, 22B and 22C illustrate respective cross sections taken along the line XXIII-CL2-XXIII in FIG. 18B, but shown as simplified.

Figure 23:
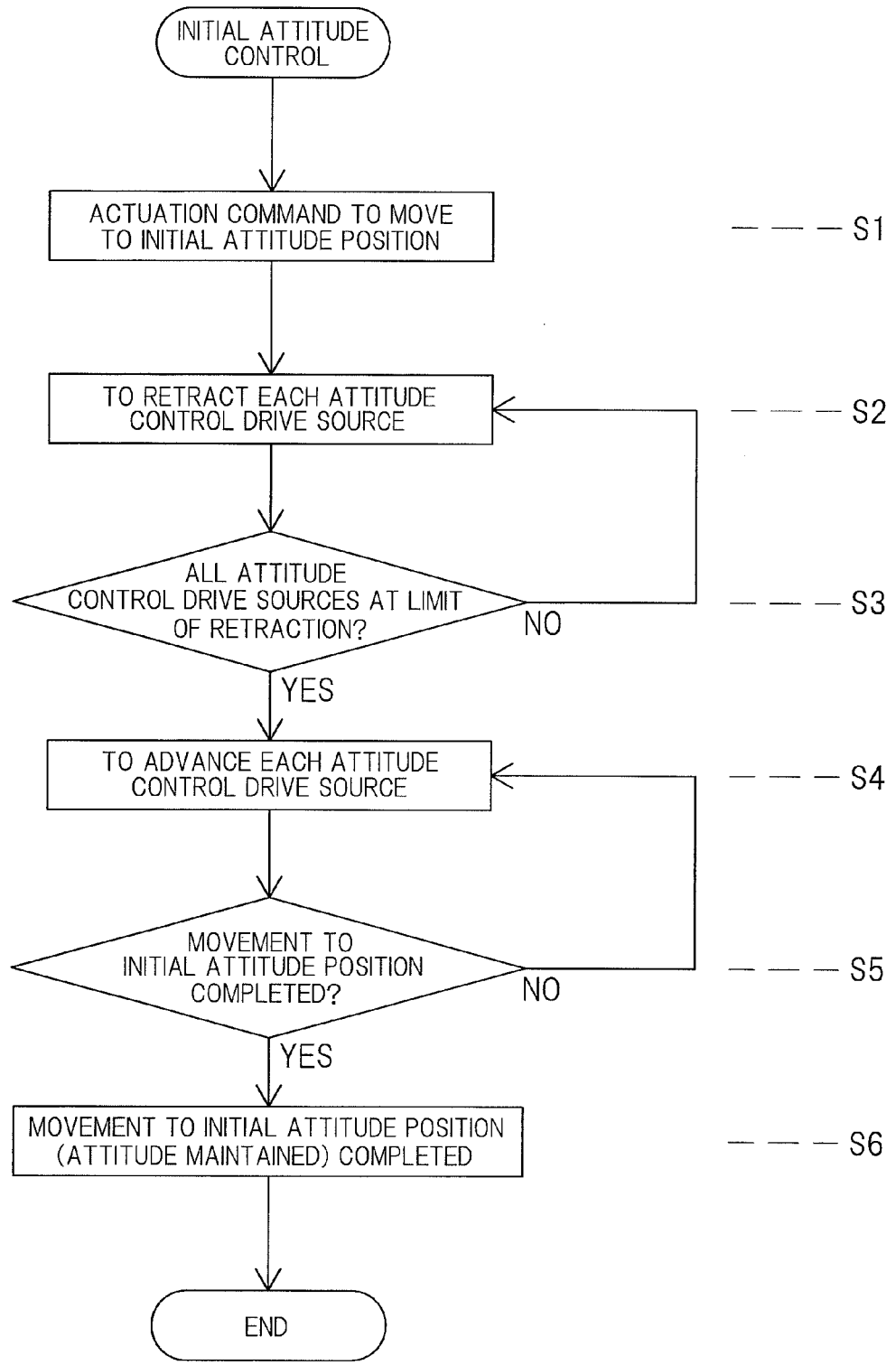
FIG. 23 is a flowchart for an initial attitude control.

The initial attitude control is carried out specifically in the sequence as shown in the flowchart of FIG. 23. When the initial attitude operating piece 87 is manipulated and the actuation command to the initial attitude position is received (at step S1), each of the attitude control drive sources 42 is retracted (at step S2). The actuation position of each of the attitude control drive sources 42 is detected by the encoder 57. Once all of the attitude control drive sources 42 are retracted to an end of retraction within the range of selective advance and retraction (at step 3), each of the attitude control drive sources 42 is advanced (at step S4). When movement of each of the attitude control drive sources 42 to the initial attitude position is completed (at step S5), advance of each of the attitude control drive sources 42 is halted and the movement to the initial attitude position completes (at step S6). Movement of each of the attitude control drive sources 42 to the initial attitude position confirms that the actual actuation position of each of the attitude control drive sources 42 indicated by the output from the encoder 57 coincides with the actuation position of each of the attitude control drive sources 42 in the initial attitude stored in the storage section 76. The progress of this initial attitude control is step by step displayed by the initial attitude control indicator lamp 86.

The tool rotation control section 71 is made up of a tool rotation control unit 71a and an emergency halt control unit 71b.

The tool rotation control unit 71a provides the motor driver 73 with an output in dependence on a rotation command signal fed from the rotation ON/OFF operating piece 84 to thereby power the tool rotation drive source 41 on or off Thereby, the spindle 13 is driven or stopped. For example, when the rotation ON/OFF operating piece 84 is pushed one time, the spindle 13 rotates, but when it is pushed next time, the spindle 13 is stopped.

The emergency halt control unit 71b performs a control to stop the rotation of the tool rotation drive source 41 in the event that an abnormality occurring during the rotation of the spindle or during the non-rotation of the spindle is detected by an abnormality detector as will be described subsequently.

The abnormality detector is a strain sensor 66 (66U, 66L and 66R) which is the locked state detector and the working force detector; an encoder 57 (57U, 57L and 57R) which is the locked state detector; a rotational speed sensor 55 which is the rotation detector; a vibration sensor 56 which is the vibration detector; a temperature sensor 16 which is the temperature detector; and a pressure sensor 82 which is the liquid lubricant pressure detector. The emergency halt control is available in the following control modes.

A first emergency halt control is a control to detect, from the output of the strain sensor 66 (66U, 66L and 66R) and the output of the encoder 57 (57U, 57L and 57R), whether or not the attitude of the distal end member 2 is locked and then to halt the rotation of the tool rotation drive source 41 in the event that the attitude of the distal end member 2 is not locked. Even though the attitude of the distal end member 2 is not actually measured, it is possible to ascertain, from the respective outputs of the strain sensor 66 and the encoder 57, whether or not the attitude of the distal end member 2 is locked. It is to be noted that this first emergency halt control may be performed simultaneously with or independent from the initial attitude control described hereinbefore.

Figure 24:
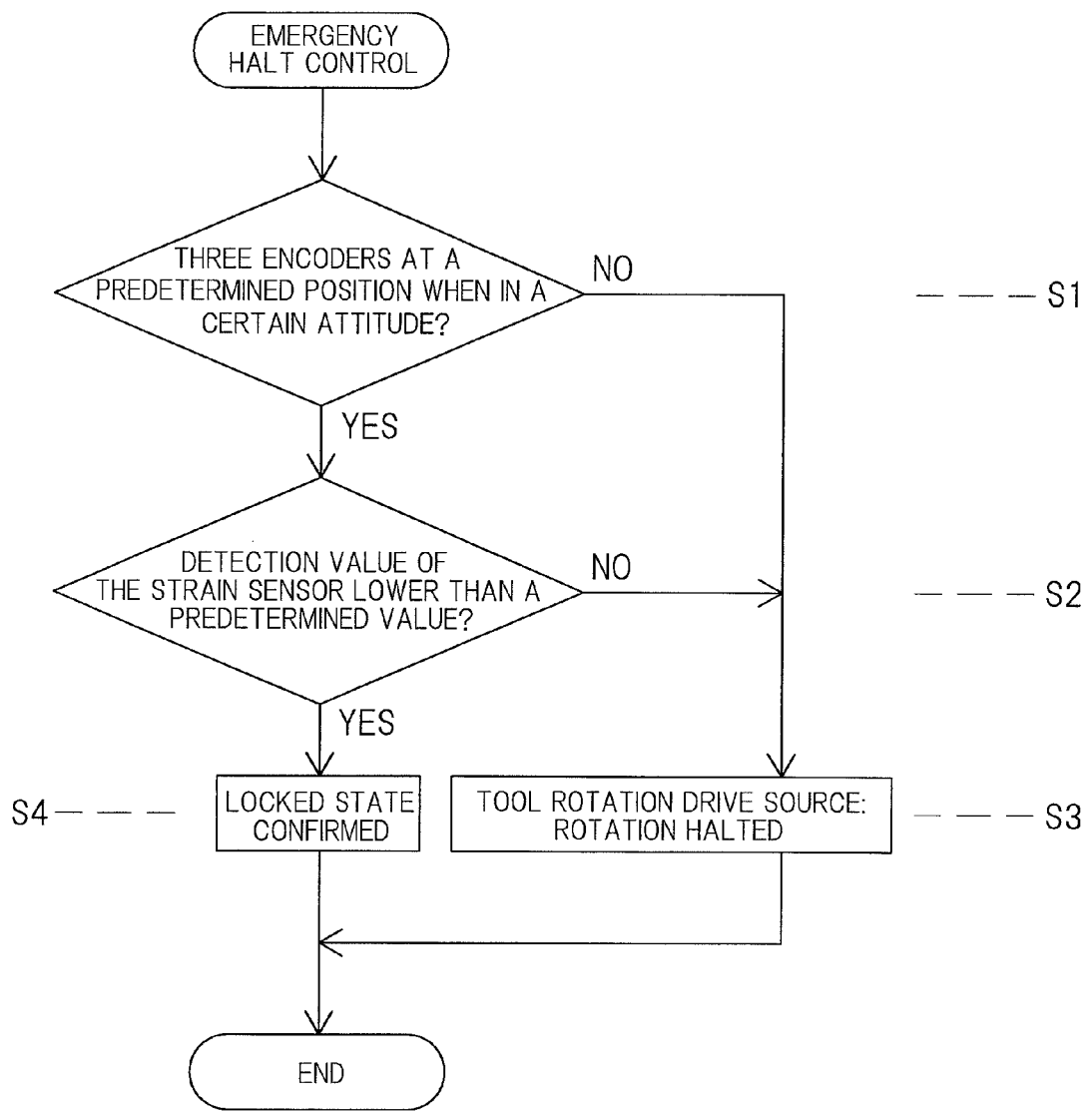
FIG. 24 is a flowchart for an abnormality halt control.

More specifically, the control is carried out in the sequence as shown in the flowchart of FIG. 24. Referring to the flowchart of FIG. 24, with the distal end member 2 held in a certain attitude, it is ascertained (at step S1) that the three encoders 57 are held at predetermined positions and, at this time, a detection value of the strain sensor 66 is determined (at step S2). If the detection value exceeds a predetermined value range, the presence of an abnormality is determined and the rotation of the tool rotation drive source 41 is then halted (at step S3). When the detection value of the strain sensor 66 is higher than a predetermined value, it means that an excessive force is acting on the attitude altering member 31. For example, as shown in FIG. 22C, there is the possibility that a foreign matter 49 may be sandwiched between the attitude altering member 31 and the distal end member 2. On the other hand, when it is lower than the predetermined value, there is the possibility that a gap S exists between the base end face of the housing 11 for the distal end member 2 and the pillar shaped pin 31b of the attitude altering member 31 as shown in FIG. 22A. Since under these conditions, the attitude altering member 31 is unable to lock the attitude of the distal end member 2 correctly, it is hazardous to rotate the spindle 13. Accordingly, the rotation of the tool rotation drive source 41 is halted. In this way, a danger can be avoided.

With the distal end member 2 held at a certain attitude, if the three encoders 57 are ascertained as held at the predetermined position and the detection value of the strain sensor 66 is within the predetermined range, the distal end member 2 is confirmed as locked (at step S4) and, hence, the control terminates.

A second emergency halt control is a control to detect the magnitude of the working force on the distal end member 2 during the rotation of the spindle from the output of the strain sensor 66 (66U, 66L and 66R) and then to halt the rotation of the tool rotation drive source 41 in the event that the working force so detected is larger than a defined working force. Even though the working force of the distal end member 2 is not actually detected, the working force of the distal end member 2 can be determined from the output of the strain sensor 66. If an excessive force acts on the distal end member 2, there is the possibility that various parts of the remote controlled actuator will be deformed and/or damaged. Accordingly, the rotation of the tool rotation drive source 41 is so halted to thereby avoid the deformation of and/or damage to the various parts of the remote controlled actuator.

A third emergency halt control is a control to detect the number of revolutions of the spindle 13 from an output of the rotational speed sensor 55 and then to halt the rotation of the tool rotation drive source 41 in the event that the difference between the number of revolutions detected and the prescribed number of revolutions is out of a predetermined range. Even though the number of revolutions of the spindle 13 is not actually detected, the number of revolutions of the spindle 13 can be determined from the output of the rotational speed sensor 55 for detecting the number of revolutions of the tool rotation drive source 41. In the event that the output shaft 41a of the tool rotation drive source 41 and/or one or some of the bearings 12, 26 and 29 used to support the rotary shaft 22 are damaged, the number of revolutions of the spindle 13 will abnormally increases or decreases. It is dangerous to allow the spindle 13 to be rotated under such a condition. Accordingly, in the event that the number of revolutions of the spindle 13 is abnormal, the rotation of the tool rotation drive source 41 is halted to avoid the danger.

A fourth emergency halt control is a control to detect the magnitude of vibration occurring in the spindle 13 from an output of the vibration sensor 56 and then to halt the rotation of the tool rotation drive source 41 in the event that the magnitude of vibration so detected is higher than a prescribed magnitude. Even though the magnitude of vibration of the spindle 13 is not actually detected, the magnitude of vibration of the spindle 13 can be determined from the output of the vibration sensor 56 for detecting the magnitude of vibration occurring in the tool rotation drive source 41. In the event that the attitude holding capability of the distal end member 2 is lowered, any trouble is found in the tool rotation drive source 41 and/or the bearings 26 and 29, and/or any defect exists in assemblage of the various parts of the remote controlled actuator, the spindle 13 accompanies vibration. It is dangerous for the spindle 13 to be rotated under such a condition. Accordingly, in the event that the magnitude of vibration occurring in the spindle 13 is abnormally high, the rotation of the tool rotation drive source 41 is halted to avoid the danger.

A fifth emergency halt control is a control to detect the temperature of the spindle 13 from an output of the temperature sensor 16 and then to halt the rotation of the tool rotation drive source 41 in the event that the temperature so detected is higher than a prescribed temperature. It may occur that the temperature of the spindle 13 may increase as a result of the lack of the lubricant used to lubricate the bearings 12, 26 and 29 and/or troubles occurring in the bearings 12, 26 and 29. If the spindle 13 is allowed to continue its rotation in such case, the remote controlled actuator will possibly be deformed or damaged. Accordingly, in the event that the temperature of the spindle 13 is abnormally high, the rotation of the tool rotation drive source 41 is halted to avoid the possible deformation of and/or damage to the remote controlled actuator.

A sixth emergency halt control is a control to detect the pressure of the liquid lubricant, supplied to the inside of the spindle guide section 3, from an output of the pressure sensor 82 and then to halt the rotation of the tool rotation drive source 41 in the event that the difference between the pressure of the liquid lubricant so detected and a prescribed pressure is out of a predetermined range. In the event of the lack of the liquid lubricant and/or clogging occurring in the path of flow of the liquid lubricant, the bearings 12, 26 and 29 will not be favorably lubricated and therefore some or all of those bearings 12, 26 and 29 will possibly be damaged. Accordingly, in the event that the pressure of the liquid lubricant is abnormally lowered as a result of the lack of the liquid lubricant, or in the event that the pressure of the liquid lubricant is abnormally increased as a result of clogging taking place in the path of flow of the liquid lubricant, the rotation of the tool rotation drive source 41 is halted to avoid the possible damages to some or all of the bearings 12, 26 and 29.

In each of the emergency halt controls discussed above, in the event that the abnormality is detected by the abnormality detector, specific particulars thereof are displayed by the display panel 85. Accordingly, even when a plurality of abnormality detector are employed such as in the embodiment now under discussion, it is possible to know what has resulted in abnormality and, therefore, a proper care or countermeasure can be quickly taken.

As hereinbefore described, the remote controlled actuator according to this embodiment is manipulated with the actuator body 8 held by hands then gripping the left and right handles 80L and 80R. With the rotation ON/OFF operating piece 84 manipulated, the spindle 13 is rotated to allow the tool 1 to undergo cutting of the bone. During the processing, manipulation of the attitude altering operation piece 83 according to the shape of a processing site and/or the progress of the processing results in change of the attitude of the distal end member 2 in the two-axis directions by remote control. Since the rotation ON/OFF operating piece 84 and the attitude altering operation piece 83 can be manipulated by hand while the left and right handles 80L and 80R are gripped, the operator can use his or her sensory perception to perform the required manipulation and as a result, the intended work can readily be accomplished.

In the event of occurrence of any abnormality during the cutting process, such abnormality is detected by the abnormality detector 16, 55, 56, 57, 66 and 82 and the tool rotation control section 71 halts the rotation of the tool rotation drive source 41. Also, in the event that any abnormality is found by the abnormality detector 57 and 66 prior to the cutting process, the tool rotation control section 71 inhibits the tool rotation drive source 41 from being rotated. For these reasons, it is safe.

Since this embodiment makes use of the rotation preventing mechanism 37 for preventing the distal end member 2 from rotating about the center line CL1 of the distal end member 2 relative to the spindle guide section 3, even when the distal end member 2 then holding the tool 1 becomes uncontrollable as a result of any trouble occurring in the attitude altering drive mechanism 4c and/or the attitude alteration control section 72, it is possible to avoid the possibility that the site to be processed may be impaired as a result of rotation of the distal end member 2 about the center line CL1 or the distal end member 2 itself is broken.

Since the attitude altering member 31 is inserted through the guide hole 30a, the attitude altering member 31 can properly act on the distal end member 2 at all times without being accompanied by displacement in position in a direction perpendicular to the lengthwise direction thereof and the attitude altering operation of the distal end member 2 can therefore be performed accurately. Also, since the attitude altering member 31 is made up of the plural balls 31c and the pillar shaped pins 31b and has a flexible property in its entirety, the attitude altering operation of the distal end member 2 is carried out accurately even though the spindle guide section 3 is curved. In addition, since the center of the junction between the spindle 13 and the rotary shaft 22 lies at the same position as the respective centers of curvature O of the guide faces F1 and F2, no force tending to press and pull will not act on the rotary shaft 22 as a result of the alteration of the attitude of the distal end member 2 and the distal end member 2 can be smoothly altered in attitude.

Although in describing the remote controlled actuator reference has been made to that for the medical use, the present invention can be equally applied to the remote controlled actuator for use in any application. By way of example, if the remote controlled actuator is used in performing a mechanical processing, a drilling process for drilling a curved hole and a cutting process to be performed at a site deep in the groove can be accomplished.

Hereinafter, some modes of application, in which the cutting force estimator 6, which has been described as an essential requirement in the foregoing embodiment or embodiments, are not required will be described.

[Mode 1]

A remote controlled actuator according to the mode 1 comprises a spindle guide section of an elongated configuration, a distal end member fitted to a distal end of the spindle guide section through a distal end member connecting unit for alteration in attitude, and a drive unit housing having a base end of the spindle guide section connected therewith;

in which the distal end member rotatably supports a spindle for holding a tool; the spindle guide section includes a rotary shaft for transmitting rotation of a tool rotation drive source, provided within the drive unit housing, to the spindle and a guide hole open defined therein so as to extend from one end to the opposite end; an attitude altering member for altering the attitude of the distal end member as a tip end thereof selectively advances or retracts in contact with the distal end member is reciprocally movably inserted within the guide hole; and an attitude altering drive source for selectively advancing or retracting the attitude altering member is provided within the drive unit housing; and in which there are provided an abnormality detector for detecting an abnormality occurring during rotation or non-rotation of the spindle and a tool rotation control section for halting the rotation of the tool rotation drive source in the event that the abnormality is detected by the abnormality detector.

[Mode 2]

In the mode 1 above, as the abnormality detector there is provided a locked state detector for detecting whether or not the distal end member is in a locked state, and the tool rotation control section inhibits the tool rotation drive source from rotating in the event that the locked state detector detects that the attitude of the distal end member is not in the locked state.

[Mode 3]

In the mode 2 above, the locked state detector comprises a strain sensor for detecting a strain occurring in a lever mechanism disposed between the attitude altering drive source and the attitude altering member.

[Mode 4]

In the mode 2 above, the locked state detector comprises an encoder for detecting an operating position of the attitude altering drive source.

[Mode 5]

In the mode 1 above, as the abnormality detector there is provided a working force detector for detecting the magnitude of a force acting on the distal end member during the rotation of the spindle, and the tool rotation control section inhibits the tool rotation drive source from rotating in the event that the working force so detected by the working force detector is higher than a prescribed working force.

[Mode 6]

In the mode 5 above, the working force detector comprises a strain sensor for detecting a strain appearing in a lever mechanism provided between the attitude altering drive source and the attitude altering member.

[Mode 7]

In the mode 1 above, as the abnormality detector there is provided a rotation detector for detecting the number of revolutions of the tool rotation drive source or the spindle, and the tool rotation control section inhibits the tool rotation drive source from rotating in the event that the difference between the number of revolutions, detected by the rotation detector, and a prescribed number of revolutions is out of a predetermined range.

[Mode 8]

In the mode 1 above, as the abnormality detector, there is provided a vibration detector for detecting the magnitude of vibration of the tool rotation drive source or the spindle during the rotation of the spindle, and the tool rotation control section inhibits the tool rotation drive source from rotating in the event that the magnitude of the vibration detected by the vibration detector is larger than a prescribed magnitude.

[Mode 9]

In the mode 1 above, as the abnormality detector there is provided a temperature detector for detecting the temperature of the spindle during the rotation of the spindle, and the tool rotation control section inhibits the tool rotation drive source from rotating in the event that the temperature detected by the temperature detector is higher than a prescribed temperature.

[Mode 10]

In the mode 1 above, there are provided a bearing for rotatably supporting the rotary shaft within the spindle guide section and a liquid lubricant supply device for supplying a liquid lubricant for lubricating the bearing to the inside of the spindle guide section, and as the abnormality detector there is provided a liquid lubricant pressure detector for detecting a pressure of the liquid lubricant supplied by the liquid lubricant supply device to the inside of the spindle guide section during the rotation of the spindle, and the tool rotation control section inhibits the tool rotation drive source from rotating in the event that the difference between the pressure of the liquid lubricant, detected by the liquid lubricant pressure detector, and a prescribed pressure is out of a predetermined range.

[Mode 11]

In the mode 1 above, the remote controlled actuator is provided with a display panel for displaying particulars of abnormality in the event that the abnormality detector detects an abnormality.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . Tool
2 . . . Distal end member
3 . . . Spindle guide section
4a . . . Drive unit housing
5 . . . Controller
6 . . . Cutting force estimator
7 . . . Control box
13 . . . Spindle
15 . . . Distal end member connecting unit
16 . . . Temperature sensor (Temperature detector)
22 . . . Rotary shaft
25 . . . Outer shell pipe
26, 29 . . . Rolling bearing
27A, 27B . . . Spring element
30 . . . Guide pipe
30a . . . Guide hole
31 . . . Attitude altering member
41 . . . Tool rotation drive source
42 . . . Attitude altering drive source
43 . . . Lever mechanism (Force transmitting mechanism)
43b . . . Lever
45 . . . Operating amount detector
46 . . . Attitude detector
48 . . . Load detector
50 . . . Cooling unit
55 . . . Rotational speed sensor (Rotation detector)
56 . . . Vibration sensor (Vibration detector)
57 (57U, 57L, 57R) . . . Encoder (Locked state detector)
60 . . . Driving power measuring section
61 . . . Rotational speed measuring section
63 . . . Flexure amount measuring section
65 . . . Driving power measuring section
66 (66U, 66L, 66R) . . . Strain sensor (Strain detector (Locked state detector, Working force detector))
70 . . . Computer
84 . . . Rotation ON/OFF operating piece
85 . . . Display panel
87 . . . Initial attitude operating piece

What is claimed is:

1. A remote controlled actuator which comprises a spindle guide section of an elongated configuration, a distal end member fitted to a distal end of the spindle guide section through a distal end member connecting unit for alteration in attitude, and a drive unit housing having a base end of the spindle guide section connected therewith;

in which the distal end member rotatably supports a spindle for holding a tool; the spindle guide section includes a rotary shaft for transmitting rotation of a tool rotation drive source, provided within the drive unit housing, to the spindle and a guide hole opening defined therein so as to extend from one end to the opposite end; an attitude altering member for altering the attitude of the distal end member as a tip end thereof selectively advances or retracts in contact with the distal end member is reciprocally movably inserted within the guide hole; and an attitude altering drive source for selectively advancing or retracting the attitude altering member is provided within the drive unit housing; and in which there is provided a cutting force estimator for estimating at least one component force of a principle force, a radial force and a feed force in a cutting force which the tool applies to a work to be processed.

2. The remote controlled actuator as claimed in claim 1, further comprising a driving power measuring section for measuring a driving power of the tool rotation drive source and a rotational speed measuring section for measuring the number of revolutions; and wherein the cutting force estimator estimates the magnitude of the at least one component force of the principle force, the radial force and the feed force in the cutting force, from the driving power, measured by the driving power measuring section, and the number of revolutions measured by the rotational speed measuring section.

3. The remote controlled actuator as claimed in claim 1, further comprising a flexure amount measuring section for measuring the amount of flexure taking place in the spindle guide section; and wherein the cutting force estimator estimates the magnitude of the at least one component force of the principle force, the radial force and the feed force in the cutting force, from the amount of flexure measured by the flexure amount measuring section.

4. The remote controlled actuator as claimed in claim 3, in which the flexure amount measuring section comprises one or more strain sensors pasted to a peripheral surface of the spindle guide section.

5. The remote controlled actuator as claimed in claim 1, further comprising a driving power measuring section for measuring a driving power of the attitude altering drive source; and wherein the cutting force estimator estimates the magnitude of the at least one component force of the principle force, the radial force and the feed force in the cutting force, from the driving power measured by the driving power measuring section.

6. The remote controlled actuator as claimed in claim 1, further comprising a lever mechanism for transmitting a driving power of the attitude altering drive source to the attitude altering member and a strain detector for detecting a strain appearing in the lever mechanism, and wherein the cutting force estimator estimates the magnitude of the at least one component force of the principle force, the radial force and the feed force in the cutting force, from a detection value of the strain detector.

7. The remote controlled actuator as claimed in claim 1, further comprising a plurality of rolling bearings for rotatably supporting the rotary shaft within the spindle guide section, and spring elements for applying a preload to those rolling bearings.

8. The remote controlled actuator as claimed in claim 1, further comprising an abnormality detector for detecting an abnormality occurring during the rotation or non-rotation of the spindle, and a tool rotation control section for halting the rotation of the tool rotation drive source in the event that the abnormality detector detects the abnormality.

9. The remote controlled actuator as claimed in claim 8, in which as the abnormality detector there is provided a locked state detector for detecting whether or not the attitude of the distal end member is in a locked state; and in which the tool rotation control section inhibits the tool rotation drive source from rotating in the event that the locked state detector detects that the attitude of the distal end member is not in the locked state.

10. The remote controlled actuator as claimed in claim 9, in which the locked state detector comprises a strain sensor for detecting a strain occurring in a lever mechanism disposed between the attitude altering drive source and the attitude altering member.

11. The remote controlled actuator as claimed in claim 8, in which as the abnormality detector there is provided a working force detector for detecting the magnitude of a force acting on the distal end member during the rotation of the spindle; and in which the tool rotation control section inhibits the tool rotation drive source from rotating in the event that the working force detected by the working force detector is higher than a prescribed working force.

12. The remote controlled actuator as claimed in claim 8, in which as the abnormality detector there is provided a rotation detector for detecting the number of revolutions of the spindle or the tool rotation drive source; and in which the tool rotation control section inhibits the tool rotation drive source from rotating in the event that the difference between the number of revolutions, detected by the rotation detector, and a prescribed number of revolutions is out of a predetermined range.

13. The remote controlled actuator as claimed in claim 8, in which as the abnormality detector there is provided a vibration detector for detecting the magnitude of vibration of the tool rotation drive source or the spindle during the rotation of the spindle; and wherein the tool rotation control section inhibits the tool rotation drive source from rotating in the event that the magnitude of the vibration detected by the vibration detector is larger than a prescribed magnitude.

14. The remote controlled actuator as claimed in claim 8, in which as the abnormality detector there is provided a temperature detector for detecting the temperature of the spindle during the rotation of the spindle; and wherein the tool rotation control section inhibits the tool rotation drive source from rotating in the event that the temperature detected by the temperature detector is higher than a prescribed temperature.

15. The remote controlled actuator as claimed in claim 8, further comprising:

a bearing for rotatably supporting the rotary shaft within the spindle guide section;

a liquid lubricant supply device for supplying a liquid lubricant for lubricating the bearing to the inside of the spindle guide section; and a liquid lubricant pressure detector, as the abnormality detector, for detecting the pressure of the liquid lubricant supplied by the liquid lubricant supply device to the inside of the spindle guide section during the rotation of the spindle; and wherein the tool rotation control section inhibits the tool rotation drive source from rotating in the event that the difference between the pressure of the liquid lubricant, detected by the liquid lubricant pressure detector, and a prescribed pressure is out of a predetermined range.

* * * * *